US005667997A

United States Patent [19]

Voelker et al.

[11] Patent Number: 5,667,997

[45] Date of Patent: Sep. 16, 1997

[54] C8 AND C10 MEDIUM-CHAIN THIOESTERASES IN PLANTS

[75] Inventors: Toni Alois Voelker; Huw Maelor Davies, both of Davis; Deborah Knutzon, Granite Bay, all of Calif.

[73] Assignee: Calgene, Inc., Davis, Calif.

[21] Appl. No.: 424,406

[22] PCT Filed: Oct. 29, 1993

[86] PCT No.: PCT/US93/10814

§ 371 Date: Jul. 5, 1995

§ 102(e) Date: Jul. 5, 1995

[87] PCT Pub. No.: WO94/10288

PCT Pub. Date: May 11, 1994

Related U.S. Application Data

[63] Continuation-in-part of Ser. No. 968,971, Oct. 30, 1992, Pat. No. 5,455,167.

[51] Int. Cl.$^{6}$ .............................. C12N 5/10; C12N 15/29; C12N 15/63

[52] U.S. Cl. .................................... 435/172.3; 435/320.1; 435/252.3; 435/325; 435/419

[58] Field of Search .............................. 435/320.1, 240.1, 435/240.4, 172.3, 252.3, 325, 419; 800/205, DIG. 15, DIG. 16, DIG. 17

[56] References Cited

U.S. PATENT DOCUMENTS 5,512,482 4/1996 Voelker et al. ...................... 435/320.1

FOREIGN PATENT DOCUMENTS 9506740 3/1995 WIPO .

OTHER PUBLICATIONS

U.S. application No. 08/467098, Voelker et al., filed Jun. 6, 1995.

Naggert, et al (1987) Biochem. J. 243: 597–601.

Poulose, et al (1985) Journal of Biol. Chem. 260 (29); 15953–15958.

Pollard et al in The Metabolism, Structure, & Function of Plant Lipids, pp. 455–463, 1987.

Gasser, et al (Jun. 1989) Science 244: 1293–1299.

*Primary Examiner*—Che S. Chereskin

[57] ABSTRACT

By this invention, further plant medium-chain acyl-ACP thioesterases are provided, as well as uses of long-chain thioesterase sequences in conjunction with medium-chain thioesterase sequences. In a first embodiment, this invention relates to particular medium-chain thioesterase sequences from elm and Cuphea, and to DNA constructs for the expression of these thioesterases in host cells for production of C8 and C10 fatty acids. Other aspects of this invention relate to methods for using plant medium-chain thioesterases or medium-chain thioesterases from non-plant sources to provide medium-chain fatty acids in plant cells. As a further aspect, uses of long-chain thioesterase sequences for anti-sense methods in plant cells in conjunction with expression of medium-chain thioesterases in plant cells is described.

20 Claims, 40 Drawing Sheets

```
AGAGAGAGAG AGAGAGAGAG AGCTAAATTA AAAAAAAAAC CCAGAAGTGG GAAATCTTCC   60

CCATGAAATA ACGGATCCTC TTGCTACTGC TACTACTACT ACTACAAACT GTAGCCATTT  120

ATATAATTCT ATATAATTTT CAAC ATG GCC ACC ACC TCT TTA GCT TCC GCT TTC 174
                           Met Ala Thr Thr Ser Leu Ala Ser Ala Phe
                            1               5                  10

TGC TCG ATG AAA GCT GTA ATG TTG GCT CGT GAT GGC CGG GGC ATG AAA     222
Cys Ser Met Lys Ala Val Met Leu Ala Arg Asp Gly Arg Gly Met Lys
                15                  20                  25

CCC AGG AGC AGT GAT TTG CAG CTG AGG GCG GGA AAT GCG CCA ACC TCT     270
Pro Arg Ser Ser Asp Leu Gln Leu Arg Ala Gly Asn Ala Pro Thr Ser
            30                  35                  40

TTG AAG ATG ATC AAT GGG ACC AAG TTC AGT TAC ACG GAG AGC TTG AAA     318
Leu Lys Met Ile Asn Gly Thr Lys Phe Ser Tyr Thr Glu Ser Leu Lys
        45                  50                  55

AGG TTG CCT GAC TGG AGC ATG CTC TTT GCA GTG ATC ACA ACC ATC TTT     366
Arg Leu Pro Asp Trp Ser Met Leu Phe Ala Val Ile Thr Thr Ile Phe
    60                  65                  70
```

FIG. 1A

```
TCG GCT GCT GAG AAG CAG TGG ACC AAT CTA GAG TGG AAG CCG AAG CCG    414
Ser Ala Ala Glu Lys Gln Trp Thr Asn Leu Glu Trp Lys Pro Lys Pro
75                  80                  85                  90

AAG CTA CCC CAG TTG CTT GAT GAC CAT TTT GGA CTG CAT GGG TTA GTT    462
Lys Leu Pro Gln Leu Leu Asp Asp His Phe Gly Leu His Gly Leu Val
                95                  100                 105

TTC AGG CGC ACC TTT GCC ATC AGA TCT TAT GAG GTG GGA CCT GAC CGC    510
Phe Arg Arg Thr Phe Ala Ile Arg Ser Tyr Glu Val Gly Pro Asp Arg
            110                 115                 120

TCC ACA TCT ATA CTG GCT GTT ATG AAT CAC ATG CAG GAG GCT ACA CTT    558
Ser Thr Ser Ile Leu Ala Val Met Asn His Met Gln Glu Ala Thr Leu
        125                 130                 135

AAT CAT GCG AAG AGT GTG GGA ATT CTA GGA GAT GGA TTC GGG ACG ACG    606
Asn His Ala Lys Ser Val Gly Ile Leu Gly Asp Gly Phe Gly Thr Thr
    140                 145                 150

CTA GAG ATG AGT AAG AGA GAT CTG ATG TGG GTT GTG AGA CGC ACG CAT    654
Leu Glu Met Ser Lys Arg Asp Leu Met Trp Val Val Arg Arg Thr His
155                 160                 165                 170
```

FIG. 1B

```
GTT GCT GTG GAA CGG TAC CCT ACT TGG GGT GAT ACT GTA GAA GTA GAG     702
Val Ala Val Glu Arg Tyr Pro Thr Trp Gly Asp Thr Val Glu Val Glu
                175                 180                 185

TGC TGG ATT GGT GCA TCT GGA AAT AAT GGC ATG CGA CGT GAT TTC CTT     750
Cys Trp Ile Gly Ala Ser Gly Asn Asn Gly Met Arg Arg Asp Phe Leu
            190                 195                 200

GTC CGG GAC TGC AAA ACA GGC GAA ATT CTT ACA AGA TGT ACC AGC CTT     798
Val Arg Asp Cys Lys Thr Gly Glu Ile Leu Thr Arg Cys Thr Ser Leu
        205                 210                 215

TCG GTG CTG ATG AAT ACA AGG ACA AGG AGG TTG TCC ACA ATC CCT GAC     846
Ser Val Leu Met Asn Thr Arg Thr Arg Arg Leu Ser Thr Ile Pro Asp
    220                 225                 230

GAA GTT AGA GGG GAG ATA GGG CCT GCA TTC ATT GAT AAT GTG GCT GTC     894
Glu Val Arg Gly Glu Ile Gly Pro Ala Phe Ile Asp Asn Val Ala Val
235                 240                 245                 250

AAG GAC GAT GAA ATT AAG AAA CTA CAG AAG CTC AAT GAC AGC ACT GCA     942
Lys Asp Asp Glu Ile Lys Lys Leu Gln Lys Leu Asn Asp Ser Thr Ala
                255                 260                 265
```

FIG. 1C

```
GAT TAC ATC CAA GGA GGT TTG ACT CCT CGA TGG AAT GAT TTG GAT GTC    990
Asp Tyr Ile Gln Gly Gly Leu Thr Pro Arg Trp Asn Asp Leu Asp Val
            270                 275                 280

AAT CAG CAT GTG AAC AAC CTC AAA TAC GTT GCC TGG GTT TTT GAG ACC   1038
Asn Gln His Val Asn Asn Leu Lys Tyr Val Ala Trp Val Phe Glu Thr
        285                 290                 295

GTC CCA GAC TCC ATC TTT GAG AGT CAT CAT ATT TCC AGC TTC ACT CTT   1086
Val Pro Asp Ser Ile Phe Glu Ser His His Ile Ser Ser Phe Thr Leu
    300                 305                 310

GAA TAC AGG AGA GAG TGC ACG AGG GAT AGC GTG CTG CGG TCC CTG ACC   1134
Glu Tyr Arg Arg Glu Cys Thr Arg Asp Ser Val Leu Arg Ser Leu Thr
315                 320                 325                 330

ACT GTC TCT GGT GGC TCG TCG GAG GCT GGG TTA GTG TGC GAT CAC TTG   1182
Thr Val Ser Gly Gly Ser Ser Glu Ala Gly Leu Val Cys Asp His Leu
                335                 340                 345

CTC CAG CTT GAA GGT GGG TCT GAG GTA TTG AGG GCA AGA ACA GAG TGG   1230
Leu Gln Leu Glu Gly Gly Ser Glu Val Leu Arg Ala Arg Thr Glu Trp
            350                 355                 360
```

FIG. 1D

```
AGG CCT AAG CTT ACC GAT AGT TTC AGA GGG ATT AGT GTG ATA CCC GCA    1278
Arg Pro Lys Leu Thr Asp Ser Phe Arg Gly Ile Ser Val Ile Pro Ala
        365                 370                 375

GAA CCG AGG GTG TAACTAATGA AAGAAGCATC TGTTGAAGTT TCTCCCATGC        1330
Glu Pro Arg Val
    380

TGTTCGTGAG GATACTTTTT AGAAGCTGCA GTTTGCATTG CTTGTGCAGA ATCATGGTCT 1390

GTGGTTTTAG ATGTATATAA AAAATAGTCC TGTAGTCATG AAACTTAATA TCAGAAAAAT 1450

AACTCAATGG GTCAAGGTTA TCGAAGTAGT CATTTAAGCT TTGAAATATG TTTTGTATTC 1510

CTCGGCTTAA TCTGTAAGCT CTTTCTCTTG CAATAAAGTT CGCCTTTCAA T           1561
```

FIG. 1E

```
GAA TTC GGC ACG AGG GGC TCC GGT GCT TTG CAG GTG AAG GCA AGT TCC      48
Glu Phe Gly Thr Arg Gly Ser Gly Ala Leu Gln Val Lys Ala Ser Ser
                 5                  10                  15

CAA GCT CCA CCA AAG CTC AAT GGT TCC AAT GTG GGT TTG GTT AAA TCT      96
Gln Ala Pro Pro Lys Leu Asn Gly Ser Asn Val Gly Leu Val Lys Ser
             20                  25                  30

AGC CAA ATT GTG AAG AAG GGT GAT GAC ACC ACA TCT CCT CCT GCA AGA     144
Ser Gln Ile Val Lys Lys Gly Asp Asp Thr Thr Ser Pro Pro Ala Arg
         35                  40                  45

ACT TTC ATC AAC CAA TTG CCT GAT TGG AGC ATG CTT CTT GCT GCT ATC     192
Thr Phe Ile Asn Gln Leu Pro Asp Trp Ser Met Leu Leu Ala Ala Ile
     50                  55                  60

ACA ACC CTG TTC TTG GCT GCA GAG AAG CAG TGG ATG ATG CTT GAT TGG     240
Thr Thr Leu Phe Leu Ala Ala Glu Lys Gln Trp Met Met Leu Asp Trp
65                  70                  75                  80

AAA CCC AAA AGG CCT GAC ATG CTT GTT GAT CCA TTT GGT CTT GGA AGG     288
Lys Pro Lys Arg Pro Asp Met Leu Val Asp Pro Phe Gly Leu Gly Arg
                 85                  90                  95

TTT GTT CAG GAT GGT CTT GTT TTC CGC AAC AAC TTT TCA ATT CGA TCA     336
Phe Val Gln Asp Gly Leu Val Phe Arg Asn Asn Phe Ser Ile Arg Ser
            100                 105                 110
```

FIG. 2A

```
TAT GAA ATA GGG GCT GAT CGA ACG GCT TCT ATA GAA ACG TTA ATG AAT     384
Tyr Glu Ile Gly Ala Asp Arg Thr Ala Ser Ile Glu Thr Leu Met Asn
        115                 120                 125

CAT CTG CAG GAA ACA GCT CTT AAT CAT GTG AAG TCT GTT GGG CTT CTT     432
His Leu Gln Glu Thr Ala Leu Asn His Val Lys Ser Val Gly Leu Leu
    130                 135                 140

GAG GAT GGC CTA GGT TCG ACT CGA GAG ATG TCC TTG AGG AAC CTG ATA     480
Glu Asp Gly Leu Gly Ser Thr Arg Glu Met Ser Leu Arg Asn Leu Ile
145                 150                 155                 160

TGG GTT GTC ACT AAA ATG CAG GTT GCG GTT GAT CGC TAT CCA ACT TGG     528
Trp Val Val Thr Lys Met Gln Val Ala Val Asp Arg Tyr Pro Thr Trp
                165                 170                 175

GGA GAT GAA GTT CAG GTA TCC TCT TGG GCT ACT GCA ATT GGA AAG AAT     576
Gly Asp Glu Val Gln Val Ser Ser Trp Ala Thr Ala Ile Gly Lys Asn
            180                 185                 190

GGA ATG CGT CGC GAA TGG ATA GTC ACT GAT TTT AGA ACT GGT GAA ACT     624
Gly Met Arg Arg Glu Trp Ile Val Thr Asp Phe Arg Thr Gly Glu Thr
        195                 200                 205

CTA TTA AGA GCC ACC AGT GTT TGG GTG ATG ATG AAT AAA CTG ACG AGG     672
Leu Leu Arg Ala Thr Ser Val Trp Val Met Met Asn Lys Leu Thr Arg
    210                 215                 220
```

FIG. 2B

```
AGG ATA TCC AAA ATC CCA GAA GAG GTT TGG CAC GAA ATA GGC CCC TCT    720
Arg Ile Ser Lys Ile Pro Glu Glu Val Trp His Glu Ile Gly Pro Ser
225                 230                 235                 240

TTC ATT GAT GCT CCT CCT CTT CCC ACC GTG GAA GAT GAT GGT AGA AAG    768
Phe Ile Asp Ala Pro Pro Leu Pro Thr Val Glu Asp Asp Gly Arg Lys
                245                 250                 255

CTG ACA AGG TTT GAT GAA AGT TCT GCA GAC TTT ATC CGC NCT GGT TTA    816
Leu Thr Arg Phe Asp Glu Ser Ser Ala Asp Phe Ile Arg Xxx Gly Leu
            260                 265                 270

ACT CCT AGG TGG AGT GAT TTG GAC ATC AAC CAG CAT GTC AAC AAT GTG    864
Thr Pro Arg Trp Ser Asp Leu Asp Ile Asn Gln His Val Asn Asn Val
        275                 280                 285

AAG TAC ATT GGC TGG CTC CTT GAG AGT GCT CCG CCG GAG ATC CAC GAG    912
Lys Tyr Ile Gly Trp Leu Leu Glu Ser Ala Pro Pro Glu Ile His Glu
    290                 295                 300

AGT CAC GAG ATA GCG TCT CTG ACT CTG GAG TAC AGG AGG GAG TGT GGA    960
Ser His Glu Ile Ala Ser Leu Thr Leu Glu Tyr Arg Arg Glu Cys Gly
305                 310                 315                 320

AGG GAC AGC GTG CTG AAC TCC GCG ACC AAG GTC TCT GAC TCC TCT CAA   1008
Arg Asp Ser Val Leu Asn Ser Ala Thr Lys Val Ser Asp Ser Ser Gln
                325                 330                 335
```

FIG. 2C

```
CTG GGA AAG TCT GCT GTG GAG TGT AAC CAC TTG GTT CGT CTC CAG AAT   1056
Leu Gly Lys Ser Ala Val Glu Cys Asn His Leu Val Arg Leu Gln Asn
            340                 345                 350

GGT GGG GAG ATT GTG AAG GGA AGG ACT GTG TGG AGG CCC AAA CGT CCT   1104
Gly Gly Glu Ile Val Lys Gly Arg Thr Val Trp Arg Pro Lys Arg Pro
        355                 360                 365

CTT TAC AAT GAT GGT GCT GTT GTG GAC GTG NAA GCT AAA ACC TCT       1149
Leu Tyr Asn Asp Gly Ala Val Val Asp Val Xxx Ala Lys Thr Ser
    370                 375                 380

TAAGTCTTAT AGTCCAAGTG AGGAGGAGTT CTATGTATCA GGAAGTTGCT AGGATTCTCA 1209

ATCGCATGTG TCCATTTCTT GTGTGGAATA CTGCTCGTGT TTCTAGACTC GCTATATGTT 1269

TGTTCTTTTA TATATATATA TATATATATA TCTCTCTCTT CCCCCCACCT CTCTCTCTCT 1329

CTCTATATAT ATATATGTTT TATGTAAGTT TTCCCCTTAG TTTCCTTTCC TAAGTAATGC 1389

CATTGTAAAT TACTTCAAAA AAAAAAAAAA AAAAAAAACT CGAG                  1433
```

FIG. 2D

```
TGGATCC AAT CAA CAT GTC AAC AAT GTG AAA TAC ATT GGG TGG ATT CTC     49
        Asn Gln His Val Asn Asn Val Lys Tyr Ile Gly Trp Ile Leu
         1               5                  10

AAG AGT GTT CCA ACA AAA GTT TTC GAG ACC CAG GAG TTA TGT GGC GTC     97
Lys Ser Val Pro Thr Lys Val Phe Glu Thr Gln Glu Leu Cys Gly Val
 15                  20                  25                  30

ACC CTC GAG TAC CGG CGG GAA TGC TCGAG                               126
Thr Leu Glu Tyr Arg Arg Glu Cys
                 35
```

FIG. 3

CUPHEA-14-2

AATCAACATG TCAACAATGT GAAATACATT GGGTGGATTC TCAAGAGTGT TCCAACAAAA 60

GTTTTCGAGA CCCAGGAGTT ATGTGGCGTC ACCCTCGAGT ACCGGCGGGA ATGC 114

CUPHEA-14-9

AATCAGCATG TGAATAACGT GAAATACATT GGGTGGATTC TCAAGAGTGT TCCAACAGAT 60

GTTTTTGAGG CCCAGGAGCT ATGTGGAGTC ACCCTCGAG 99

FIG. 4

```
ACGCGGTGGC GGCCGCTCTA GAACTAGTGG ATCCCCCGGG CTGCAGGAAT TCGGCACGAG   60
CTTTCTCCCC CACAACCTCT TTCCCGCATT TGTTGAGCTG TTTTTTGTCG CCATTCGCCC  120
TCTCCTCTTC AGTTCAACGA AAATGGTGGC TACCCTGCAA GTTCTGCATT CTTCCCCCTG  180
CCATCCGCCG ACACCTCCTC TTCGAGACCC GGAAAGCTCG GCAATGGGCC ATCGAGCTTC  240
AGCCCCCTCA AGCCCAAATC GACCCCCAAT GGCGGTTTGC AGGTTAAGGC AAACGCCAGC  300
GCCCCTCCTA AGATCAATGG TTCACCGGTC GGTCTAAAGT CGGGCGGTCT CAAGACTCAG  360
GAAGACGCTC CTTCGGCCCC TCCTCCGCGG ACTTTTATCA ACCAGTTGCC TGATTGGAGT  420
ATGCTTCTTG CTGCAATCAC TACTGTCTTC TTGGCTGCAG AGAAGCAGTG GATGATG CTT 480
                                                              Leu
                                                               1

GAT TGG AAA CCT AAG AGG CCT GAC ATG CTT GTG GAC CCG TTC GGA TTG    528
Asp Trp Lys Pro Lys Arg Pro Asp Met Leu Val Asp Pro Phe Gly Leu
             5                  10                  15

GGA AGT ATT GTT CAG GAT GGG CTT GTG TTC AGG CAG AAT TTT TCG ATT    576
Gly Ser Ile Val Gln Asp Gly Leu Val Phe Arg Gln Asn Phe Ser Ile
        20                  25                  30
```

FIG. 5A

```
AGG TCC TAT GAA ATA GGC GCC GAT CGC ACT GCG TCT ATA GAG ACG GTG    624
Arg Ser Tyr Glu Ile Gly Ala Asp Arg Thr Ala Ser Ile Glu Thr Val
    35                  40                      45

ATG AAC CAT TTG CAG GAA ACA GCT CTC AAT CAT GTT AAG ATT GCT GGG    672
Met Asn His Leu Gln Glu Thr Ala Leu Asn His Val Lys Ile Ala Gly
50                  55                      60                  65

CTT TCT AAT GAC GGC TTT GGT CGT ACT CCT GAG ATG TAT AAA AGG GAC    720
Leu Ser Asn Asp Gly Phe Gly Arg Thr Pro Glu Met Tyr Lys Arg Asp
                70                      75                  80

CTT ATT TGG GTT GTT GCA AAA ATG CAG GTC ATG GTT AAC CGC TAT CCT    768
Leu Ile Trp Val Val Ala Lys Met Gln Val Met Val Asn Arg Tyr Pro
            85                      90                      95

ACT TGG GGT GAC ACG GTT GAA GTG AAT ACT TGG GTT GCC AAG TCA GGG    816
Thr Trp Gly Asp Thr Val Glu Val Asn Thr Trp Val Ala Lys Ser Gly
        100                     105                     110

AAA AAT GGT ATG CGT CGT GAC TGG CTC ATA AGT GAT TGT AAT ACT GGA    864
Lys Asn Gly Met Arg Arg Asp Trp Leu Ile Ser Asp Cys Asn Thr Gly
    115                     120                     125
```

FIG. 5B

```
GAG ATT CTT ACA AGA GCA TCA AGC GTG TGG GTC ATG ATG AAT CAA AAG    912
Glu Ile Leu Thr Arg Ala Ser Ser Val Trp Val Met Met Asn Gln Lys
130                 135                 140                 145

ACA AGA AGA TTG TCA AAA ATT CCA GAT GAG GTT CGA AAT GAG ATA GAG    960
Thr Arg Arg Leu Ser Lys Ile Pro Asp Glu Val Arg Asn Glu Ile Glu
                150                 155                 160

CCT CAT TTT GTG GAC TCT CCT CCC GTC ATT GAA GAT GAT GAC CGG AAA   1008
Pro His Phe Val Asp Ser Pro Pro Val Ile Glu Asp Asp Asp Arg Lys
            165                 170                 175

CTT CCC AAG CTG GAT GAG AAG ACT GCT GAC TCC ATC CGC AAG GGT CTA   1056
Leu Pro Lys Leu Asp Glu Lys Thr Ala Asp Ser Ile Arg Lys Gly Leu
        180                 185                 190

ACT CCG AGG TGG AAT GAC TTG GAT GTC AAT CAG CAC GTC AAC AAC GTG   1104
Thr Pro Arg Trp Asn Asp Leu Asp Val Asn Gln His Val Asn Asn Val
    195                 200                 205
```

FIG. 5C

```
AAG TAC ATC GGG TGG ATT CTT GAG AGT ACT CCA CCA GAA GTT CTG GAG    1152
Lys Tyr Ile Gly Trp Ile Leu Glu Ser Thr Pro Pro Glu Val Leu Glu
210                 215                 220                 225

ACA CAG GAG TTA TGT TCC CTT ACC CTG GAA TAC AGG CGG GAA TGT GGA    1200
Thr Gln Glu Leu Cys Ser Leu Thr Leu Glu Tyr Arg Arg Glu Cys Gly
                230                 235                 240

AAG GAG AGT GTT CTG GAG TCC CTC ACT GCT ATG GAC CCC TCT GGA GGG    1248
Lys Glu Ser Val Leu Glu Ser Leu Thr Ala Met Asp Pro Ser Gly Gly
            245                 250                 255

GGC TAT GGG TCC CAG TTT CAG CAC CTT CTG CGG CTT GAG GAT GGA GGT    1296
Gly Tyr Gly Ser Gln Phe Gln His Leu Leu Arg Leu Glu Asp Gly Gly
        260                 265                 270

GAG ATC GTG AAG GGG AGA ACC GAG TGG CGA ACC CAA GAA TGG TGT AAT    1344
Glu Ile Val Lys Gly Arg Thr Glu Trp Arg Thr Gln Glu Trp Cys Asn
    275                 280                 285
```

FIG. 5D

```
CAA TGG GGT GGT ACC AAC CGG GGA GTC CTC GCC TGG AGA CTA CTC TTA   1392
Gln Trp Gly Gly Thr Asn Arg Gly Val Leu Ala Trp Arg Leu Leu Leu
290                 395                 300                 305

GAA GGG GGA GCC CTG ACC CCT TTG GAG TTA TGC TTT CTT TAT TGT CGG   1440
Glu Gly Gly Ala Leu Thr Pro Leu Glu Leu Cys Phe Leu Tyr Cys Arg
                310                 315                 320

ACG AGC TGAGTGAAGG GCAGGTAAGA TAGTAGCAAT CGGTAGATTG TGTAGTTTGT    1496
Thr Ser

TTGCTGCTTT TCACGATGGC TCTCGTGTAT AATATCATGG TCGTCTTCTT TGTATCCTCT 1556

TCGCATGTTC CGGGTTGATT TATACATTAT ATTCTTTCTA AAAAA                 1601
```

FIG. 5E

```
CTTTGATCGG TCGATCCTTT CCTCTCGCTC ATAATTTACC CATTAGTCCC CTTTGCCTTC    60

TTTAAACCCT CCTTTCCTTT CTCTTCCCTT CTTCCTCTCT GGGAAGTTTA AAGCTTTTGC   120

CTTTCTCCCC CCCACAACCT CTTTCCCGCA TTTGTTGAGC TGTTTTTTTG TCGCCATTCG   180

TCCTCTCCTC TTCAGTTCAA CAGAA ATG GTG GCT ACC GCT GCA AGT TCT GCA     232
                            Met Val Ala Thr Ala Ala Ser Ser Ala
                             1               5

TTC TTC CCC CTC CCA TCC GCC GAC ACC TCA TCG AGA CCC GGA AAG CTC     280
Phe Phe Pro Leu Pro Ser Ala Asp Thr Ser Ser Arg Pro Gly Lys Leu
10                  15                  20                  25

GGC AAT AAG CCA TCG AGC TTG AGC CCC CTC AAG CCC AAA TCG ACC CCC     328
Gly Asn Lys Pro Ser Ser Leu Ser Pro Leu Lys Pro Lys Ser Thr Pro
                30                  35                  40

AAT GGC GGT TTG CAG GTT AAG GCA AAT GCC AGT GCC CCT CCT AAG ATC     376
Asn Gly Gly Leu Gln Val Lys Ala Asn Ala Ser Ala Pro Pro Lys Ile
            45                  50                  55
```

FIG. 6A

```
AAT GGT TCC CCG GTC GGT CTA AAG TCG GGC GGT CTC AAG ACT CAG GAA     424
Asn Gly Ser Pro Val Gly Leu Lys Ser Gly Gly Leu Lys Thr Gln Glu
         60                  65                  70

GAC GCT CAT TCG GCC CCT CCT CCG CGA ACT TTT ATC AAC CAG TTG CCT     472
Asp Ala His Ser Ala Pro Pro Pro Arg Thr Phe Ile Asn Gln Leu Pro
     75                  80                  85

GAT TGG AGT ATG CTT CTT GCT GCA ATC ACG ACT GTC TTC TTG GCT GCA     520
Asp Trp Ser Met Leu Leu Ala Ala Ile Thr Thr Val Phe Leu Ala Ala
 90                  95                 100                 105

GAG AAG CAA TGG ATG ATG CTT GAT TGG AAA CCT AAG AGG CCT GAC ATG     568
Glu Lys Gln Trp Met Met Leu Asp Trp Lys Pro Lys Arg Pro Asp Met
                110                 115                 120

CTT GTG GAC CCG TTT GGA TTG GGA AGT ATT GTT CAG GAT GGG CTT GTG     616
Leu Val Asp Pro Phe Gly Leu Gly Ser Ile Val Gln Asp Gly Leu Val
            125                 130                 135

TTC AGG CAG AAT TTT TCG ATT AGG TCC TAT GAA ATA GGC GCC GAT CGC     664
Phe Arg Gln Asn Phe Ser Ile Arg Ser Tyr Glu Ile Gly Ala Asp Arg
        140                 145                 150
```

FIG. 6B

```
ACT GCG TCT ATA GAG ACG GTG ATG AAC CAT TTG CAG GAA ACA GCT CTC     712
Thr Ala Ser Ile Glu Thr Val Met Asn His Leu Gln Glu Thr Ala Leu
    155                 160                 165

AAT CAT GTT AAG ATT GCT GGG CTT TCT AAT GAC GGC TTT GGT CGT ACT     760
Asn His Val Lys Ile Ala Gly Leu Ser Asn Asp Gly Phe Gly Arg Thr
170                 175                 180                 185

CCT GAG ATG TAT AAA AGG GAC CTT ATT TGG GTT GTT GCG AAA ATG CAA     808
Pro Glu Met Tyr Lys Arg Asp Leu Ile Trp Val Val Ala Lys Met Gln
                190                 195                 200

GTC ATG GTT AAC CGC TAT CCT ACT TGG GGT GAC ACG GTT GAA GTG AAT     856
Val Met Val Asn Arg Tyr Pro Thr Trp Gly Asp Thr Val Glu Val Asn
            205                 210                 215

ACT TGG GTT GCC AAG TCA GGG AAA AAT GGT ATG CGT CGT GAC TGG CTC     904
Thr Trp Val Ala Lys Ser Gly Lys Asn Gly Met Arg Arg Asp Trp Leu
        220                 225                 230

ATA AGT GAT TGC AAT ACT GGA GAG ATT CTT ACA AGA GCA TCA AGC GTG     952
Ile Ser Asp Cys Asn Thr Gly Glu Ile Leu Thr Arg Ala Ser Ser Val
    235                 240                 245
```

FIG. 6C

```
TGG GTC ATG ATG AAT CAA AAG ACA AGA AGA TTG TCA AAA ATT CCA GAT   1000
Trp Val Met Met Asn Gln Lys Thr Arg Arg Leu Ser Lys Ile Pro Asp
250                 255                 260                 265

GAG GTT CGA AAT GAG ATA GAG CCT CAT TTT GTG GAC TCT CCT CCC GTC   1048
Glu Val Arg Asn Glu Ile Glu Pro His Phe Val Asp Ser Pro Pro Val
                270                 275                 280

ATT GAA GAC GAT GAC CGG AAA CTT CCC AAG CTG GAT GAG AAG ACT GCT   1096
Ile Glu Asp Asp Asp Arg Lys Leu Pro Lys Leu Asp Glu Lys Thr Ala
            285                 290                 295

GAC TCC ATC CGC AAG GGT CTA ACT CCG AGG TGG AAT GAC TTG GAT GTC   1144
Asp Ser Ile Arg Lys Gly Leu Thr Pro Arg Trp Asn Asp Leu Asp Val
        300                 305                 310

AAT CAA CAC GTC AAC AAC GTG AAG TAC ATC GGG TGG ATT CTT GAG AGT   1192
Asn Gln His Val Asn Asn Val Lys Tyr Ile Gly Trp Ile Leu Glu Ser
    315                 320                 325

ACT CCA CCA GAA GTT CTG GAG ACC CAG GAG TTA TGT TCC CTT ACT CTG   1240
Thr Pro Pro Glu Val Leu Glu Thr Gln Glu Leu Cys Ser Leu Thr Leu
330                 335                 340                 345
```

FIG. 6D

```
GAA TAC AGG CGG GAA TGT GGA AGG GAG AGC GTG CTG GAG TCC CTC ACT    1288
Glu Tyr Arg Arg Glu Cys Gly Arg Glu Ser Val Leu Glu Ser Leu Thr
                350                 355                 360

GCT ATG GAT CCC TCT GGA GGG GGT TAT GGG TCC CAG TTT CAG CAC CTT    1336
Ala Met Asp Pro Ser Gly Gly Gly Tyr Gly Ser Gln Phe Gln His Leu
            365                 370                 375

CTG CGG CTT GAG GAT GGA GGT GAG ATC GTG AAG GGG AGA ACT GAG TGG    1384
Leu Arg Leu Glu Asp Gly Gly Glu Ile Val Lys Gly Arg Thr Glu Trp
        380                 385                 390

CGG CCC AAG AAT GGT GTA ATC AAT GGG GTG GTA CCA ACC GGG GAG TCC    1432
Arg Pro Lys Asn Gly Val Ile Asn Gly Val Val Pro Thr Gly Glu Ser
    395                 400                 405

TCA CCT GGA GAC TAC TCT TAGAAGGGAG CCCTGACCCC TTTGGAGTTG           1480
Ser Pro Gly Asp Tyr Ser
410                 415

TGATTTCTTT ATTGTCGGAC GAGCTAAGTG AAGGGCAGGT AAGATAGTAG CAATCGGTAG 1540

ATTGTGTAGT TTGTTTGCTG CTTTTTCACG ATGGCTCTCG TGTATAATAT CATGGTCTGT 1600
```

FIG. 6E

CTTCTTTGTA TCCTCTTCTT CGCATGTTCC GGGTTGATTC ATACATTATA TTCTTTCTAT 1660

TTGTTTGAAG GCGAGTAGCG GGTTGTAATT ATTTATTTTG TCATTACAAT GTCGTTTAAC 1720

TTTTCAAATG AAACTACTTA TGTG 1744

FIG. 6F

```
CTGGATACCA TTTTCCCTGC GAAAAAAC ATG GTG GCT GCT GCA GCA AGT TCC      52
                               Met Val Ala Ala Ala Ala Ser Ser
                                1               5

GCA TTC TTC CCT GTT CCA GCC CCG GGA GCC TCC CCT AAA CCC GGG AAG    100
Ala Phe Phe Pro Val Pro Ala Pro Gly Ala Ser Pro Lys Pro Gly Lys
    10                  15                  20

TTC GGA AAT TGG CCC TCG AGC TTG AGC CCT TCC TTC AAG CCC AAG TCA    148
Phe Gly Asn Trp Pro Ser Ser Leu Ser Pro Ser Phe Lys Pro Lys Ser
25                  30                  35                  40

ATC CCC AAT GGC GGA TTT CAG GTT AAG GCA AAT GAC AGC GCC CAT CCA    196
Ile Pro Asn Gly Gly Phe Gln Val Lys Ala Asn Asp Ser Ala His Pro
                45                  50                  55

AAG GCT AAC GGT TCT GCA GTT AGT CTA AAG TCT GGC AGC CTC AAC ACT    244
Lys Ala Asn Gly Ser Ala Val Ser Leu Lys Ser Gly Ser Leu Asn Thr
            60                  65                  70

CAG GAG GAC ACT TCG TCG TCC CCT CCT CCT CGG ACT TTC CTT CAC CAG    292
Gln Glu Asp Thr Ser Ser Ser Pro Pro Pro Arg Thr Phe Leu His Gln
        75                  80                  85
```

FIG. 7A

```
TTG CCT GAT TGG AGT AGG CTT CTG ACT GCA ATC ACG ACC GTG TTC GTG     340
Leu Pro Asp Trp Ser Arg Leu Leu Thr Ala Ile Thr Thr Val Phe Val
    90                  95                  100

AAA TCT AAG AGG CCT GAC ATG CAT GAT CGG AAA TCC AAG AGG CCT GAC     388
Lys Ser Lys Arg Pro Asp Met His Asp Arg Lys Ser Lys Arg Pro Asp
105                 110                 115                 120

ATG CTG GTG GAC TCG TTT GGG TTG GAG AGT ACT GTT CAG GAT GGG CTC     436
Met Leu Val Asp Ser Phe Gly Leu Glu Ser Thr Val Gln Asp Gly Leu
                125                 130                 135

GTG TTC CGA CAG AGT TTT TCG ATT AGG TCT TAT GAA ATA GGC ACT GAT     484
Val Phe Arg Gln Ser Phe Ser Ile Arg Ser Tyr Glu Ile Gly Thr Asp
            140                 145                 150

CGA ACG GCC TCT ATA GAG ACA CTT ATG AAC CAC TTG CAG GAA ACA TCT     532
Arg Thr Ala Ser Ile Glu Thr Leu Met Asn His Leu Gln Glu Thr Ser
        155                 160                 165

CTC AAT CAT TGT AAG AGT ACC GGT ATT CTC CTT GAC GGC TTC GGT CGT     580
Leu Asn His Cys Lys Ser Thr Gly Ile Leu Leu Asp Gly Phe Gly Arg
    170                 175                 180
```

FIG. 7B

```
ACT CTT GAG ATG TGT AAA AGG GAC CTC ATT TGG GTG GTA ATA AAA ATG     628
Thr Leu Glu Met Cys Lys Arg Asp Leu Ile Trp Val Val Ile Lys Met
185                 190                 195                 200

CAG ATC AAG GTG AAT CGC TAT CCA GCT TGG GGC GAT ACT GTC GAG ATC     676
Gln Ile Lys Val Asn Arg Tyr Pro Ala Trp Gly Asp Thr Val Glu Ile
                205                 210                 215

AAT ACC CGG TTC TCC CGG TTG GGG AAA ATC GGT ATG GGT CGC GAT TGG     724
Asn Thr Arg Phe Ser Arg Leu Gly Lys Ile Gly Met Gly Arg Asp Trp
            220                 225                 230

CTA ATA AGT GAT TGC AAC ACA GGA GAA ATT CTT GTA AGA GCT ACG AGC     772
Leu Ile Ser Asp Cys Asn Thr Gly Glu Ile Leu Val Arg Ala Thr Ser
        235                 240                 245

GCG TAT GCC ATG ATG AAT CAA AAG ACG AGA AGA CTC TCA AAA CTT CCA     820
Ala Tyr Ala Met Met Asn Gln Lys Thr Arg Arg Leu Ser Lys Leu Pro
    250                 255                 260

TAC GAG GTT CAC CAG GAG ATA GTG CCT CTT TTT GTC GAC TCT CCT GTC     868
Tyr Glu Val His Gln Glu Ile Val Pro Leu Phe Val Asp Ser Pro Val
265                 270                 275                 280
```

FIG. 7C

```
ATT GAA GAC AGT GAT CTG AAA GTG CAT AAG TTT AAA GTG AAG ACT GGT     916
Ile Glu Asp Ser Asp Leu Lys Val His Lys Phe Lys Val Lys Thr Gly
                285                 290                 295

GAT TCC ATT CAA AAG GGT CTA ACT CCG GGG TGG AAT GAC TTG GAT GTC     964
Asp Ser Ile Gln Lys Gly Leu Thr Pro Gly Trp Asn Asp Leu Asp Val
            300                 305                 310

AAT CAG CAC GTA AGC AAC GTG AAG TAC ATT GGG TGG ATT CTC GAG AGT    1012
Asn Gln His Val Ser Asn Val Lys Tyr Ile Gly Trp Ile Leu Glu Ser
        315                 320                 325

ATG CCA ACA GAA GTT TTG GAG ACC CAG GAG CTA TGC TCT CTC GCC CTT    1060
Met Pro Thr Glu Val Leu Glu Thr Gln Glu Leu Cys Ser Leu Ala Leu
    330                 335                 340

GAA TAT AGG CGG GAA TGC GGA AGG GAC AGT GTG CTG GAG TCC GTG ACC    1108
Glu Tyr Arg Arg Glu Cys Gly Arg Asp Ser Val Leu Glu Ser Val Thr
345                 350                 355                 360

GCT ATG GAT CCC TCA AAA GTT GGA GTC CGT TCT CAG TAC CAG CAC CTT    1156
Ala Met Asp Pro Ser Lys Val Gly Val Arg Ser Gln Tyr Gln His Leu
                365                 370                 375
```

FIG. 7D

```
CTG CGG CTT GAG GAT GGG ACT GCT ATC GTG AAC GGT GCA ACT GAG TGG     1204
Leu Arg Leu Glu Asp Gly Thr Ala Ile Val Asn Gly Ala Thr Glu Trp
            380                 385                 390

CGG CCG AAG AAT GCA GGA GCT AAC GGG GCG ATA TCA ACG GGA AAG ACT     1252
Arg Pro Lys Asn Ala Gly Ala Asn Gly Ala Ile Ser Thr Gly Lys Thr
        395                 400                 405

TCA AAT GGA AAC TCG GTC TCT TAGAAGTGTC TCGGAACCCT TCCGAGATGT        1303
Ser Asn Gly Asn Ser Val Ser
    410                 415

GCATTTCTTT TCTCCTTTTC ATTTTGTGGT GAGCTGAAAG AAGAGCATGT CGTTGCAATC 1363

AGTAAATTGT GTAGTTCGTT TTTCGCTTTG CTTCGCTCCT TTGTATAATA ATATGGTCAG 1423

TCGTCTTTGT ATCATTTCAT GTTTTCAGTT TATTTACGCC ATATAATTTT T           1474
```

FIG. 7E

```
GGCACGAGAA ACATGGTGGC TGCCGCAGCA AGTTCTGCAT TCTTCTCCGT TCCAACCCCG   60
GGAATCTCCC CTAAACCCGG GAAGTTCGGT AATGGTGGCT TTCAGGTTAA GGCAAACGCC  120
AATGCCCATC CTAGTCTAAA GTCTGGCAGC CTCGAGACTG AAGATGACAC TTCATCGTCG  180
TCCCCTCCTC CTCGGACTTT CATTAACCAG TTGCCCGACT GGAGTATGCT TCTGTCCGCA  240
ATCACGACTA TCTTCGGGGC AGCTGAGAAG CAGTGGATGA TGCTTGATAG GAAATCTAAG  300
NAGACCCGAC ATGCTCATGG CAACCGTTTG GGGTTGACAG TATTGTTCAG GATGGGGTTT  360
TTTTCAGACA GAGTTTTTCG ATTAGATCTT ACGAAATAGG CGCTGATCGA ACAACCTCAA  420
TAGAGACGCT GATGAACATG TTCCAGGAAA CGTCTTTGAA TCATTGTAAG AGTAACGGTC  480
TTCTCAATGA CGGCTTTGGT CGCACTCCTG AGATGTGTAA GAAGGGCCTC ATTTGGGTGG  540
TTACGAAAAT GCAGGTCGAG GTGAATCGCT ATCCTATTTG GSGTGATTCT ATCGAAGTCA  600
ATACTTGGGT CTCCGAGTCG GGGNAAAANC GGTATGGGTC GTGATTGGCT GATAAGTGAT  660
```

FIG.8A

```
TGCAGTACAG GAGNAAATTC TTGTAAGAGC AACGAGCGTG TGGGCTATGA TGAATCAAAA  720

GACGAGAAGA TTGTCAAAAT TTCCATTTGA GGTTCGACAA GAGATAGCGC CTAATTTTGT  780

CGACTCTGTT CCTGTCATTG AAGACGATCG AAAATTACAC AAGCTTGATG TGAAGACGGG  840

TGATTCCATT CACAATGGTC TAACTCCAAG GTGGAATGAC TTGGATGTCA ATCAGCACGT  900

TAACAATGTG AAATACATTG GGTGGATTCT CAAGAGTGTT CCAACAGATG TTTTTGGGGC  960

CCAGGAGCTA TGTGGA                                                 976
```

FIG. 8B

```
GAATTCGGCA CGAGTCTCTC TCTCTCTCTC TCTCTCTCTC TCTCTCTCTC TCTCTCTCTC   60
TCTCCCCAAC GAAATTTCAA TTCCATTAGC TGTTGACAAA AACAGCTGAA GATCACAAAT  120
TTGTTCTCAG AGGAAGAAAA GGAAGGAAGG AAGGAAGGAG GAGGAAGCCA TTGTGGGCAA  180
TATTTGATCG GTGGATCCTT TCCTCCCGCT CGTTGAAAGA CAATGGTGGC TACCGCTGCA  240
AGCTCTGCAT TCTTCCCCGT GTCGTCCCCG GTCACCTCCT CTAGACCAGG AAAGCCCGGA  300
AATGGGTCAT CGAGCTTCAG CCCCATCAAG CCCAAATTTG TCGCCAATGG CGGGTTGCAG  360
GTTAAGGCAA ACGCCAGTGC CCCTCCTAAG ATCAATGGTT CCTCGGTCGG TCTAAAGTCC  420
TGCAGTCTCA AGACTCAGGA AGACACTCCT TCGGCCCCTG CTCCACGGAC TTTTATCAAC  480
CAGTTGCCTG ATTGGAGTAT GCTTCTTGCT GCAATTACTA CTGTCTTCTT GGCAGCAGAG  540
AAGCAGTGGA TGATGCTTGA TTGGAAACCT AAGAGGCCTG ACATGCTTGT GGACCCGTTC  600
GGATTGGGAA GTATTGTCCA GCATGGGCTT GTGTTCAGGC AGAATTTTTC GATTAGGTCC  660
```

FIG.9A

TATGAAATAG GCGCTGATCG CACTGCGTCT ATAGAGACGG TGATGAACCA CTTGCAGGAA 720

ACGGCTCTCA ATCATGTTAA GAGTGCGGGG CTTATGAATG ACGGCTTTGG TCGTACTCCT 780

GAGATGTATA AAAAGGACCT TATTTGGGTT GTCGCGAAAA TGCAGGTCAT GGTTAACCGC 840

TATCCTACTT GGGGTGACAC AGTTGAAGTG AATACTTGGG TTGCCAAGTC AGGGAAAAAT 900

GGTATGCGTC GTGATTGGCT CATAAGTGAT TGTAATACAG GAGAAATTCT TACTAGAGCA 960

TCAAGCGTGT GGGTCATGAT GAATCAAAAG ACAAGAAGAT TGTCAAAAAT TCCAGATGAG 1020

GTTCGGCATG AGATTGAGCC TCATTTTGTG GACTCTCCTC CCGTCATTGA AGACGATGAC 1080

CGAAAACTTC CCAAGCTGGA TGACAAGACT GCTGACTCCA TCCGCAAGGG TCTAACTCCG 1140

AAGTGGAATG ACTTGGATGT CAATCAGCAC GTCAACAACG TGAAGTACAT CGGGTGGATT 1200

CTTGAGAGTA CTCCACAAGA AGTTCTGGAG ACCCAGGAGC TATGTTCCCT TACCCTGGAA 1260

FIG. 9B

```
TACAGGCGGG AATGCGGAAG GGAGAGCGTG CTGGAGTCCC TCACTGCTGC GGACCCCTCT 1320

GGAAAGGGCT TTGGGTCCCA GTTCCAGCAC CTTCTGAGGC TTGAGGATGG AGGGGAGATT 1380

GTGAAGGGGA GAACTGAGTG GCGACCAAAG ACTGCAGGTA TCAATGGGGC GATACCATCC 1440

GGGGAGACCT CACCTGGAGA CTCTTAGAAG GGAGCCCTGG TCCCTTTGGA GTTCTGCTTT 1500

CTTTATGGTC GGATGAGCTG AGTGAACTGC AGGTAAGGTA GTAGCAATCG GTAGATTGTT 1560

TAGTTTGTTT GCTGTTTTTT ACTCCGGCTC TCTTTTATAA TGTCATGGTC TCATTTGTAT 1620

CCTCACATGT TTCGGGTTGA TTTATACAAT ATATTATTTC TATTTGTTTC            1670
```

FIG. 9C

```
GGCACGAGTG CCTCTTCTCC ATCTCGTCCT CCCCACATAC TGAGCCACCC AGAGAGAGAA   60

CCCAGCCGCT GTTCCCTCGG AA ATG TTG AAG CTT TCT TGC AAT GCC GCC ACC   112
                         Met Leu Lys Leu Ser Cys Asn Ala Ala Thr
                          1               5                  10

GAC CAG ATT CTG TCG TCG GCC GTG GCT CAA ACC GCA TTA TGG GGT CAA   160
Asp Gln Ile Leu Ser Ser Ala Val Ala Gln Thr Ala Leu Trp Gly Gln
                15                  20                  25

CCC AGA AAC AGA TCC TTT TCA ATG TCC GCC CGG AGA AGG GGA GCC GTT   208
Pro Arg Asn Arg Ser Phe Ser Met Ser Ala Arg Arg Arg Gly Ala Val
            30                  35                  40

TGC TGC GCG CCT CCA GCT GCT GGA AAG CCC CCT GCC ATG ACC GCT GTT   256
Cys Cys Ala Pro Pro Ala Ala Gly Lys Pro Pro Ala Met Thr Ala Val
        45                  50                  55

ATC CCA AAA GAC GGG GTG GCC TCG TCC GGG TCC GGC AGC CTG GCC GAC   304
Ile Pro Lys Asp Gly Val Ala Ser Ser Gly Ser Gly Ser Leu Ala Asp
    60                  65                  70

CAG CTG AGG CTC GGG AGC CGT ACG CAG AAT GGG CTG TCG TAC ACG GAG   352
Gln Leu Arg Leu Gly Ser Arg Thr Gln Asn Gly Leu Ser Tyr Thr Glu
75                  80                  85                  90
```

FIG. 10A

```
AAG TTC ATT GTC AGG TGC TAC GAG GTC GGT ATT AAC AAG ACA GCC ACT     400
Lys Phe Ile Val Arg Cys Tyr Glu Val Gly Ile Asn Lys Thr Ala Thr
                 95                 100                 105

GTC GAA ACC ATG GCC AAT CTC TTG CAG GAA GTA GGT TGT AAC CAT GCT     448
Val Glu Thr Met Ala Asn Leu Leu Gln Glu Val Gly Cys Asn His Ala
            110                 115                 120

CAG AGT GTT GGA TTC TCA ACT GAC GGG TTT GCG ACG ACG CCT ACC ATG     496
Gln Ser Val Gly Phe Ser Thr Asp Gly Phe Ala Thr Thr Pro Thr Met
        125                 130                 135

AGG AAA TTG AAT CTG ATA TGG GTT ACT GCT CGA ATG CAC ATA GAA ATT     544
Arg Lys Leu Asn Leu Ile Trp Val Thr Ala Arg Met His Ile Glu Ile
    140                 145                 150

TAT AAG TAC CCA GCA TGG AGT GAT GTG GTT GAA ATC GAG ACT TGG TGC     592
Tyr Lys Tyr Pro Ala Trp Ser Asp Val Val Glu Ile Glu Thr Trp Cys
155                 160                 165                 170

CAA AGT GAA GGA AGA ATC GGA ACA AGA AGG GAT TGG ATT CTC AAG GAT     640
Gln Ser Glu Gly Arg Ile Gly Thr Arg Arg Asp Trp Ile Leu Lys Asp
                175                 180                 185
```

FIG. 10B

```
TAT GGT AAT GGT GAA GTT ATT GGA AGA GCC ACA AGC AAG TGG GTG ATG    688
Tyr Gly Asn Gly Glu Val Ile Gly Arg Ala Thr Ser Lys Trp Val Met
            190                 195                 200

ATG AAC CAG AAC ACT AGA CGA CTC CAA AAA GTT GAT GAT TCC GTT CGA    736
Met Asn Gln Asn Thr Arg Arg Leu Gln Lys Val Asp Asp Ser Val Arg
        205                 210                 215

GAA GAG TAT ATG GTT TTC TGT CCA CGC GAA CCA AGG TTA TCA TTT CCT    784
Glu Glu Tyr Met Val Phe Cys Pro Arg Glu Pro Arg Leu Ser Phe Pro
    220                 225                 230

GAA GAG AAC AAT CGG AGT TTG AGA AAA ATA TCT AAA TTG GAA GAT CCT    832
Glu Glu Asn Asn Arg Ser Leu Arg Lys Ile Ser Lys Leu Glu Asp Pro
235                 240                 245                 250

GCT GAG TAT TCG AGA CTT GGT CTT ACG CCT AGA AGA GCT GAT CTG GAT    880
Ala Glu Tyr Ser Arg Leu Gly Leu Thr Pro Arg Arg Ala Asp Leu Asp
                255                 260                 265

ATG AAC CAG CAT GTC AAC AAC GTT GCT TAC ATA GGT TGG GCT CTG GAG    928
Met Asn Gln His Val Asn Asn Val Ala Tyr Ile Gly Trp Ala Leu Glu
            270                 275                 280
```

FIG. 10C

```
AGT GTA CCT CAA GAA ATA ATC GAC TCT TAT GAG CTG GAA ACT ATC ACT     976
Ser Val Pro Gln Glu Ile Ile Asp Ser Tyr Glu Leu Glu Thr Ile Thr
        285                 290                 295

CTG GAC TAC AGA AGA GAA TGC CAA CAG GAT GAC GTA GTC GAT TCG CTC    1024
Leu Asp Tyr Arg Arg Glu Cys Gln Gln Asp Asp Val Val Asp Ser Leu
    300                 305                 310

ACC AGT GTT CTG TCA GAT GAG GAA TCA GGA ACA TTA CCA GAG CTC AAG    1072
Thr Ser Val Leu Ser Asp Glu Glu Ser Gly Thr Leu Pro Glu Leu Lys
315                 320                 325                 330

GGA ACA AAT GGA TCT GCA TCC ACC CCA CTG AAA CGT GAC CAT GAT GGC    1120
Gly Thr Asn Gly Ser Ala Ser Thr Pro Leu Lys Arg Asp His Asp Gly
                335                 340                 345

TCT CGC CAG TTC TTG CAC TTG CTG AGG CTC TCC CCC GAC GGG CTA GAA    1168
Ser Arg Gln Phe Leu His Leu Leu Arg Leu Ser Pro Asp Gly Leu Glu
            350                 355                 360

ATA AAC CGT GGC CGA ACT GAA TGG AGA AAG AAA TCC ACG AAA            1210
Ile Asn Arg Gly Arg Thr Glu Trp Arg Lys Lys Ser Thr Lys
        365                 370                 375

TAGAGGAGTC TCTTACATCC TGCCCATCTG GTTTGATCTG CATATGGTAT TTTCCCTTGC 1270

ACGCTTTTGC TTCCTGTTTA TTTGAGTTTG ATTCAGCACC                       1310
```

FIG. 10D

```
GCTCGCCTCC CACATTTTCT TCTTCGATCC CGAAAAG ATG TTG AAG CTC TCG TGT      55
                                        Met Leu Lys Leu Ser Cys
                                         1               5

AAT GCG ACT GAT AAG TTA CAG ACC CTC TTC TCG CAT TCT CAT CAA CCG      103
Asn Ala Thr Asp Lys Leu Gln Thr Leu Phe Ser His Ser His Gln Pro
            10                  15                  20

GAT CCG GCA CAC CGG AGA ACC GTC TCC TCC GTG TCG TGC TCT CAT CTG      151
Asp Pro Ala His Arg Arg Thr Val Ser Ser Val Ser Cys Ser His Leu
        25                  30                  35

AGG AAA CCG GTT CTC GAT CCT TTG CGA GCG ATC GTA TCT GCT GAT CAA      199
Arg Lys Pro Val Leu Asp Pro Leu Arg Ala Ile Val Ser Ala Asp Gln
    40                  45                  50

GGA AGT GTG ATT CGA GCA GAA CAA GGT TTG GGC TCA CTC GCG GAT CAG      247
Gly Ser Val Ile Arg Ala Glu Gln Gly Leu Gly Ser Leu Ala Asp Gln
55                  60                  65                  70

CTC CGA TTG GGT AGC TTG ACG GAG GAT GGT TTG TCG TAT AAG GAG AAG      295
Leu Arg Leu Gly Ser Leu Thr Glu Asp Gly Leu Ser Tyr Lys Glu Lys
                75                  80                  85

TTC ATC GTC AGA TCC TAC GAA GTG GGG AGT AAC AAG ACC GCC ACT GTC      343
Phe Ile Val Arg Ser Tyr Glu Val Gly Ser Asn Lys Thr Ala Thr Val
            90                  95                  100
```

FIG. 11A

```
GAA ACC GTC GCT AAT CTT TTG CAG GAG GTG GGA TGT AAT CAT GCG CAG     391
Glu Thr Val Ala Asn Leu Leu Gln Glu Val Gly Cys Asn His Ala Gln
        105                 110                 115

AGC GTT GGA TTC TCG ACT GAT GGG TTT GCG ACA ACA CCG ACC ATG AGG     439
Ser Val Gly Phe Ser Thr Asp Gly Phe Ala Thr Thr Pro Thr Met Arg
    120                 125                 130

AAA CTG CAT CTC ATT TGG GTC ACT GCG AGA ATG CAT ATA GAG ATC TAC     487
Lys Leu His Leu Ile Trp Val Thr Ala Arg Met His Ile Glu Ile Tyr
135                 140                 145                 150

AAG TAC CCT GCT TGG GGT GAT GTG GTT GAG ATA GAG ACA TGG TGT CAG     535
Lys Tyr Pro Ala Trp Gly Asp Val Val Glu Ile Glu Thr Trp Cys Gln
                155                 160                 165

AGT GAA GGA AGG ATC GGG ACT AGG CGT GAT TGG ATT CTT AAG GAT GTT     583
Ser Glu Gly Arg Ile Gly Thr Arg Arg Asp Trp Ile Leu Lys Asp Val
            170                 175                 180

GCT ACG GGT GAA GTC ACT GGC CGT GCT ACA AGC AAG TGG GTG ATG ATG     631
Ala Thr Gly Glu Val Thr Gly Arg Ala Thr Ser Lys Trp Val Met Met
        185                 190                 195

AAC CAA GAC ACA AGA CGG CTT CAG AAA GTT TCT GAT GAT GTT CGG GAC     679
Asn Gln Asp Thr Arg Arg Leu Gln Lys Val Ser Asp Asp Val Arg Asp
    200                 205                 210
```

FIG. 11B

```
GAG TAC TTG GTC TTC TGT CCT AAA GAA CTC AGA TTA GCA TTT CCT GAG    727
Glu Tyr Leu Val Phe Cys Pro Lys Glu Leu Arg Leu Ala Phe Pro Glu
215                 220                 225                 230

GAG AAT AAC AGA AGC TTG AAG AAA ATT CCG AAA CTC GAA GAT CCA GCT    775
Glu Asn Asn Arg Ser Leu Lys Lys Ile Pro Lys Leu Glu Asp Pro Ala
                235                 240                 245

CAG TAT TCG ATG ATT GGG CTT AAG CCT AGA CGA GCT GAT CTC GAC ATG    823
Gln Tyr Ser Met Ile Gly Leu Lys Pro Arg Arg Ala Asp Leu Asp Met
            250                 255                 260

AAC CAG CAT GTC AAT AAT GTC ACC TAT ATT GGA TGG GTT CTT GAG AGC    871
Asn Gln His Val Asn Asn Val Thr Tyr Ile Gly Trp Val Leu Glu Ser
        265                 270                 275

ATA CCT CAA GAG ATT GTA GAC ACG CAC GAA CTT CAG GTC ATA ACT CTG    919
Ile Pro Gln Glu Ile Val Asp Thr His Glu Leu Gln Val Ile Thr Leu
    280                 285                 290

GAT TAC AGA AGA GAA TGT CAA CAA GAC GAT GTG GTG GAT TCA CTC ACC    967
Asp Tyr Arg Arg Glu Cys Gln Gln Asp Asp Val Val Asp Ser Leu Thr
295                 300                 305                 310

ACT ACC ACC TCA GAG ATT GGT GGG ACC AAT GGC TCT GCA TCA TCA GGC   1015
Thr Thr Thr Ser Glu Ile Gly Gly Thr Asn Gly Ser Ala Ser Ser Gly
                315                 320                 325
```

FIG. 11C

```
ACA CAG GGG CAA AAC GAT AGC CAG TTC TTA CAT CTC TTA AGG CTG TCT   1063
Thr Gln Gly Gln Asn Asp Ser Gln Phe Leu His Leu Leu Arg Leu Ser
            330                     335                 340

GGA GAC GGT CAG GAG ATC AAC CGC GGG ACA ACC CTG TGG AGA AAG AAG   1111
Gly Asp Gly Gln Glu Ile Asn Arg Gly Thr Thr Leu Trp Arg Lys Lys
        345                     350                 355

CCC TCC AAT CTC TAAGCCATTT CGTTCTTAAG TTTCCTCTAT CTGTGTCGCT      1163
Pro Ser Asn Leu
    360

CGATGCTTCA CGAGTCTAGT CAGGTCTCAT TTTTTTCAAT CTAAATTTGG GTTAGACTAG 1223

AGAACTGGAA TTATTGGAAT TTATGAGTTT TCGTTCTTGT TTCTGTACAA ATCTTGAGGA 1283

TTGAAGCCAA ACCCATTTCA TCTT                                        1307
```

FIG. 11D

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 1561 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:1:

```
AGAGAGAGAG AGAGAGAGAG AGCTAAATTA AAAAAAAAAC CCAGAAGTGG GAAATCTTCC    60

CCATGAAATA ACGGATCCTC TTGCTACTGC TACTACTACT ACTACAAACT GTAGCCATTT   120

ATATAATTCT ATATAATTTT CAAC ATG GCC ACC ACC TCT TTA GCT TCC GCT TTC  174
                           Met Ala Thr Thr Ser Leu Ala Ser Ala Phe
                           1               5                   10

TGC TCG ATG AAA GCT GTA ATG TTG GCT CGT GAT GGC CGG GGC ATG AAA     222
Cys Ser Met Lys Ala Val Met Leu Ala Arg Asp Gly Arg Gly Met Lys
                15                  20                  25

CCC AGG AGC AGT GAT TTG CAG CTG AGG GCG GGA AAT GCG CCA ACC TCT     270
Pro Arg Ser Ser Asp Leu Gln Leu Arg Ala Gly Asn Ala Pro Thr Ser
            30                  35                  40

TTG AAG ATG ATC AAT GGG ACC AAG TTC AGT TAC ACG GAG AGC TTG AAA     318
Leu Lys Met Ile Asn Gly Thr Lys Phe Ser Tyr Thr Glu Ser Leu Lys
        45                  50                  55
```

-continued

```
AGG TTG CCT GAC TGG AGC ATG CTC TTT GCA GTG ATC ACA ACC ATC TTT     366
Arg Leu Pro Asp Trp Ser Met Leu Phe Ala Val Ile Thr Thr Ile Phe
    60                  65                  70

TCG GCT GCT GAG AAG CAG TGG ACC AAT CTA GAG TGG AAG CCG AAG CCG     414
Ser Ala Ala Glu Lys Gln Trp Thr Asn Leu Glu Trp Lys Pro Lys Pro
75                  80                  85                  90

AAG CTA CCC CAG TTG CTT GAT GAC CAT TTT GGA CTG CAT GGG TTA GTT     462
Lys Leu Pro Gln Leu Leu Asp Asp His Phe Gly Leu His Gly Leu Val
                95                  100                 105

TTC AGG CGC ACC TTT GCC ATC AGA TCT TAT GAG GTG GGA CCT GAC CGC     510
Phe Arg Arg Thr Phe Ala Ile Arg Ser Tyr Glu Val Gly Pro Asp Arg
            110                 115                 120

TCC ACA TCT ATA CTG GCT GTT ATG AAT CAC ATG CAG GAG GCT ACA CTT     558
Ser Thr Ser Ile Leu Ala Val Met Asn His Met Gln Glu Ala Thr Leu
        125                 130                 135

AAT CAT GCG AAG AGT GTG GGA ATT CTA GGA GAT GGA TTC GGG ACG ACG     606
Asn His Ala Lys Ser Val Gly Ile Leu Gly Asp Gly Phe Gly Thr Thr
    140                 145                 150

CTA GAG ATG AGT AAG AGA GAT CTG ATG TGG GTT GTG AGA CGC ACG CAT     654
Leu Glu Met Ser Lys Arg Asp Leu Met Trp Val Val Arg Arg Thr His
155                 160                 165                 170

GTT GCT GTG GAA CGG TAC CCT ACT TGG GGT GAT ACT GTA GAA GTA GAG     702
Val Ala Val Glu Arg Tyr Pro Thr Trp Gly Asp Thr Val Glu Val Glu
                175                 180                 185

TGC TGG ATT GGT GCA TCT GGA AAT AAT GGC ATG CGA CGT GAT TTC CTT     750
Cys Trp Ile Gly Ala Ser Gly Asn Asn Gly Met Arg Arg Asp Phe Leu
            190                 195                 200

GTC CGG GAC TGC AAA ACA GGC GAA ATT CTT ACA AGA TGT ACC AGC CTT     798
Val Arg Asp Cys Lys Thr Gly Glu Ile Leu Thr Arg Cys Thr Ser Leu
        205                 210                 215

TCG GTG CTG ATG AAT ACA AGG ACA AGG AGG TTG TCC ACA ATC CCT GAC     846
Ser Val Leu Met Asn Thr Arg Thr Arg Arg Leu Ser Thr Ile Pro Asp
    220                 225                 230

GAA GTT AGA GGG GAG ATA GGG CCT GCA TTC ATT GAT AAT GTG GCT GTC     894
Glu Val Arg Gly Glu Ile Gly Pro Ala Phe Ile Asp Asn Val Ala Val
235                 240                 245                 250

AAG GAC GAT GAA ATT AAG AAA CTA CAG AAG CTC AAT GAC AGC ACT GCA     942
Lys Asp Asp Glu Ile Lys Lys Leu Gln Lys Leu Asn Asp Ser Thr Ala
                255                 260                 265

GAT TAC ATC CAA GGA GGT TTG ACT CCT CGA TGG AAT GAT TTG GAT GTC     990
Asp Tyr Ile Gln Gly Gly Leu Thr Pro Arg Trp Asn Asp Leu Asp Val
            270                 275                 280

AAT CAG CAT GTG AAC AAC CTC AAA TAC GTT GCC TGG GTT TTT GAG ACC    1038
Asn Gln His Val Asn Asn Leu Lys Tyr Val Ala Trp Val Phe Glu Thr
        285                 290                 295

GTC CCA GAC TCC ATC TTT GAG AGT CAT CAT ATT TCC AGC TTC ACT CTT    1086
Val Pro Asp Ser Ile Phe Glu Ser His His Ile Ser Ser Phe Thr Leu
    300                 305                 310

GAA TAC AGG AGA GAG TGC ACG AGG GAT AGC GTG CTG CGG TCC CTG ACC    1134
Glu Tyr Arg Arg Glu Cys Thr Arg Asp Ser Val Leu Arg Ser Leu Thr
315                 320                 325                 330

ACT GTC TCT GGT GGC TCG TCG GAG GCT GGG TTA GTG TGC GAT CAC TTG    1182
Thr Val Ser Gly Gly Ser Ser Glu Ala Gly Leu Val Cys Asp His Leu
                335                 340                 345

CTC CAG CTT GAA GGT GGG TCT GAG GTA TTG AGG GCA AGA ACA GAG TGG    1230
Leu Gln Leu Glu Gly Gly Ser Glu Val Leu Arg Ala Arg Thr Glu Trp
            350                 355                 360

AGG CCT AAG CTT ACC GAT AGT TTC AGA GGG ATT AGT GTG ATA CCC GCA    1278
Arg Pro Lys Leu Thr Asp Ser Phe Arg Gly Ile Ser Val Ile Pro Ala
        365                 370                 375
```

-continued

GAA CCG AGG GTG TAACTAATGA AAGAAGCATC TGTTGAAGTT TCTCCCATGC 1330
Glu Pro Arg Val
380

TGTTCGTGAG GATACTTTTT AGAAGCTGCA GTTTGCATTG CTTGTGCAGA ATCATGGTCT 1390

GTGGTTTTAG ATGTATATAA AAAATAGTCC TGTAGTCATG AAACTTAATA TCAGAAAAAT 1450

AACTCAATGG GTCAAGGTTA TCGAAGTAGT CATTTAAGCT TTGAAATATG TTTTGTATTC 1510

CTCGGCTTAA TCTGTAAGCT CTTTCTCTTG CAATAAAGTT CGCCTTTCAA T 1561

( 2 ) INFORMATION FOR SEQ ID NO:2:

( i ) SEQUENCE CHARACTERISTICS:
( A ) LENGTH: 1433 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:2:

GAA TTC GGC ACG AGG GGC TCC GGT GCT TTG CAG GTG AAG GCA AGT TCC 48
Glu Phe Gly Thr Arg Gly Ser Gly Ala Leu Gln Val Lys Ala Ser Ser
5 10 15

CAA GCT CCA CCA AAG CTC AAT GGT TCC AAT GTG GGT TTG GTT AAA TCT 96
Gln Ala Pro Pro Lys Leu Asn Gly Ser Asn Val Gly Leu Val Lys Ser
20 25 30

AGC CAA ATT GTG AAG AAG GGT GAT GAC ACC ACA TCT CCT CCT GCA AGA 144
Ser Gln Ile Val Lys Lys Gly Asp Asp Thr Thr Ser Pro Pro Ala Arg
35 40 45

ACT TTC ATC AAC CAA TTG CCT GAT TGG AGC ATG CTT CTT GCT GCT ATC 192
Thr Phe Ile Asn Gln Leu Pro Asp Trp Ser Met Leu Leu Ala Ala Ile
50 55 60

ACA ACC CTG TTC TTG GCT GCA GAG AAG CAG TGG ATG ATG CTT GAT TGG 240
Thr Thr Leu Phe Leu Ala Ala Glu Lys Gln Trp Met Met Leu Asp Trp
65 70 75 80

AAA CCC AAA AGG CCT GAC ATG CTT GTT GAT CCA TTT GGT CTT GGA AGG 288
Lys Pro Lys Arg Pro Asp Met Leu Val Asp Pro Phe Gly Leu Gly Arg
85 90 95

TTT GTT CAG GAT GGT CTT GTT TTC CGC AAC AAC TTT TCA ATT CGA TCA 336
Phe Val Gln Asp Gly Leu Val Phe Arg Asn Asn Phe Ser Ile Arg Ser
100 105 110

TAT GAA ATA GGG GCT GAT CGA ACG GCT TCT ATA GAA ACG TTA ATG AAT 384
Tyr Glu Ile Gly Ala Asp Arg Thr Ala Ser Ile Glu Thr Leu Met Asn
115 120 125

CAT CTG CAG GAA ACA GCT CTT AAT CAT GTG AAG TCT GTT GGG CTT CTT 432
His Leu Gln Glu Thr Ala Leu Asn His Val Lys Ser Val Gly Leu Leu
130 135 140

GAG GAT GGC CTA GGT TCG ACT CGA GAG ATG TCC TTG AGG AAC CTG ATA 480
Glu Asp Gly Leu Gly Ser Thr Arg Glu Met Ser Leu Arg Asn Leu Ile
145 150 155 160

TGG GTT GTC ACT AAA ATG CAG GTT GCG GTT GAT CGC TAT CCA ACT TGG 528
Trp Val Val Thr Lys Met Gln Val Ala Val Asp Arg Tyr Pro Thr Trp
165 170 175

GGA GAT GAA GTT CAG GTA TCC TCT TGG GCT ACT GCA ATT GGA AAG AAT 576
Gly Asp Glu Val Gln Val Ser Ser Trp Ala Thr Ala Ile Gly Lys Asn
180 185 190

GGA ATG CGT CGC GAA TGG ATA GTC ACT GAT TTT AGA ACT GGT GAA ACT 624
Gly Met Arg Arg Glu Trp Ile Val Thr Asp Phe Arg Thr Gly Glu Thr
195 200 205

CTA TTA AGA GCC ACC AGT GTT TGG GTG ATG ATG AAT AAA CTG ACG AGG 672
Leu Leu Arg Ala Thr Ser Val Trp Val Met Met Asn Lys Leu Thr Arg

-continued

```
        210                       215                       220

AGG ATA TCC AAA ATC CCA GAA GAG GTT TGG CAC GAA ATA GGC CCC TCT     720
Arg Ile Ser Lys Ile Pro Glu Glu Val Trp His Glu Ile Gly Pro Ser
225                     230                     235                 240

TTC ATT GAT GCT CCT CCT CTT CCC ACC GTG GAA GAT GAT GGT AGA AAG     768
Phe Ile Asp Ala Pro Pro Leu Pro Thr Val Glu Asp Asp Gly Arg Lys
                245                     250                     255

CTG ACA AGG TTT GAT GAA AGT TCT GCA GAC TTT ATC CGC NCT GGT TTA     816
Leu Thr Arg Phe Asp Glu Ser Ser Ala Asp Phe Ile Arg Xxx Gly Leu
            260                     265                     270

ACT CCT AGG TGG AGT GAT TTG GAC ATC AAC CAG CAT GTC AAC AAT GTG     864
Thr Pro Arg Trp Ser Asp Leu Asp Ile Asn Gln His Val Asn Asn Val
        275                     280                     285

AAG TAC ATT GGC TGG CTC CTT GAG AGT GCT CCG CCG GAG ATC CAC GAG     912
Lys Tyr Ile Gly Trp Leu Leu Glu Ser Ala Pro Pro Glu Ile His Glu
    290                     295                     300

AGT CAC GAG ATA GCG TCT CTG ACT CTG GAG TAC AGG AGG GAG TGT GGA     960
Ser His Glu Ile Ala Ser Leu Thr Leu Glu Tyr Arg Arg Glu Cys Gly
305                     310                     315                 320

AGG GAC AGC GTG CTG AAC TCC GCG ACC AAG GTC TCT GAC TCC TCT CAA    1008
Arg Asp Ser Val Leu Asn Ser Ala Thr Lys Val Ser Asp Ser Ser Gln
                325                     330                     335

CTG GGA AAG TCT GCT GTG GAG TGT AAC CAC TTG GTT CGT CTC CAG AAT    1056
Leu Gly Lys Ser Ala Val Glu Cys Asn His Leu Val Arg Leu Gln Asn
            340                     345                     350

GGT GGG GAG ATT GTG AAG GGA AGG ACT GTG TGG AGG CCC AAA CGT CCT    1104
Gly Gly Glu Ile Val Lys Gly Arg Thr Val Trp Arg Pro Lys Arg Pro
        355                     360                     365

CTT TAC AAT GAT GGT GCT GTT GTG GAC GTG NAA GCT AAA ACC TCT        1149
Leu Tyr Asn Asp Gly Ala Val Val Asp Val Xxx Ala Lys Thr Ser
    370                     375                     380

TAAGTCTTAT AGTCCAAGTG AGGAGGAGTT CTATGTATCA GGAAGTTGCT AGGATTCTCA 1209

ATCGCATGTG TCCATTTCTT GTGTGGAATA CTGCTCGTGT TTCTAGACTC GCTATATGTT 1269

TGTTCTTTTA TATATATATA TATATATATA TCTCTCTCTT CCCCCCACCT CTCTCTCTCT 1329

CTCTATATAT ATATATGTTT TATGTAAGTT TTCCCCTTAG TTTCCTTTCC TAAGTAATGC 1389

CATTGTAAAT TACTTCAAAA AAAAAAAAAA AAAAAAAACT CGAG                  1433
```

( 2 ) INFORMATION FOR SEQ ID NO:3:

( i ) SEQUENCE CHARACTERISTICS:
( A ) LENGTH:126 base pairs
( B ) TYPE: nucleic acid
( C ) STRANDEDNESS: double
( D ) TOPOLOGY: linear ( i i ) MOLECULE TYPE:other nucleic acid
( A ) DESCRIPTION: PCR to mRNA ( x i ) SEQUENCE DESCRIPTION: SEQ ID NO:3:

```
 TGGATCC AAT CAA CAT GTC AAC AAT GTG AAA TAC ATT GGG TGG ATT CTC     49

         Asn Gln His Val Asn Asn Val Lys Tyr Ile Gly Trp Ile Leu
           1               5                  10

AAG AGT GTT CCA ACA AAA GTT TTC GAG ACC CAG GAG TTA TGT GGC GTC     97
Lys Ser Val Pro Thr Lys Val Phe Glu Thr Gln Glu Leu Cys Gly Val
 15                     20                  25                  30

ACC CTC GAG TAC CGG CGG GAA TGC TCGAG                             126
Thr Leu Glu Tyr Arg Arg Glu Cys
                35
```

-continued ( 2 ) INFORMATION FOR SEQ ID NO:4:

( i ) SEQUENCE CHARACTERISTICS:
( A ) LENGTH: 114 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: PCR to mRNA ( x i ) SEQUENCE DESCRIPTION: SEQ ID NO:4:

AATCAACATG TCAACAATGT GAAATACATT GGGTGGATTC TCAAGAGTGT TCCAACAAAA 60

GTTTTCGAGA CCCAGGAGTT ATGTGGCGTC ACCCTCGAGT ACCGGCGGGA ATGC 114

( 2 ) INFORMATION FOR SEQ ID NO:5:

( i ) SEQUENCE CHARACTERISTICS:
( A ) LENGTH: 99 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: PCR to mRNA ( x i ) SEQUENCE DESCRIPTION: SEQ ID NO:5 :

AATCAGCATG TGAATAACGT GAAATACATT GGGTGGATTC TCAAGAGTGT TCCAACAGAT 60

GTTTTTGAGG CCCAGGAGCT ATGTGGAGTC ACCCTCGAG 99

( 2 ) INFORMATION FOR SEQ ID NO:6:

( i ) SEQUENCE CHARACTERISTICS:
( A ) LENGTH: 1601 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:6:

ACGCGGTGGC GGCCGCTCTA GAACTAGTGG ATCCCCCGGG CTGCAGGAAT TCGGCACGAG 60

CTTTCTCCCC CACAACCTCT TTCCCGCATT TGTTGAGCTG TTTTTTGTCG CCATTCGCCC 120

TCTCCTCTTC AGTTCAACGA AAATGGTGGC TACCCTGCAA GTTCTGCATT CTTCCCCCTG 180

CCATCCGCCG ACACCTCCTC TTCGAGACCC GGAAAGCTCG GCAATGGGCC ATCGAGCTTC 240

AGCCCCCTCA AGCCCAAATC GACCCCCAAT GGCGGTTTGC AGGTTAAGGC AAACGCCAGC 300

GCCCCTCCTA AGATCAATGG TTCACCGGTC GGTCTAAAGT CGGGCGGTCT CAAGACTCAG 360

GAAGACGCTC CTTCGGCCCC TCCTCCGCGG ACTTTTATCA ACCAGTTGCC TGATTGGAGT 420

ATGCTTCTTG CTGCAATCAC TACTGTCTTC TTGGCTGCAG AGAAGCAGTG GATGATG CTT 480
Leu
1

GAT TGG AAA CCT AAG AGG CCT GAC ATG CTT GTG GAC CCG TTC GGA TTG 528
Asp Trp Lys Pro Lys Arg Pro Asp Met Leu Val Asp Pro Phe Gly Leu
5 10 15

GGA AGT ATT GTT CAG GAT GGG CTT GTG TTC AGG CAG AAT TTT TCG ATT 576
Gly Ser Ile Val Gln Asp Gly Leu Val Phe Arg Gln Asn Phe Ser Ile
20 25 30

AGG TCC TAT GAA ATA GGC GCC GAT CGC ACT GCG TCT ATA GAG ACG GTG 624
Arg Ser Tyr Glu Ile Gly Ala Asp Arg Thr Ala Ser Ile Glu Thr Val
35 40 45

ATG AAC CAT TTG CAG GAA ACA GCT CTC AAT CAT GTT AAG ATT GCT GGG 672
Met Asn His Leu Gln Glu Thr Ala Leu Asn His Val Lys Ile Ala Gly

-continued 50 55 60 65

CTT TCT AAT GAC GGC TTT GGT CGT ACT CCT GAG ATG TAT AAA AGG GAC 720
Leu Ser Asn Asp Gly Phe Gly Arg Thr Pro Glu Met Tyr Lys Arg Asp
70 75 80

CTT ATT TGG GTT GTT GCA AAA ATG CAG GTC ATG GTT AAC CGC TAT CCT 768
Leu Ile Trp Val Val Ala Lys Met Gln Val Met Val Asn Arg Tyr Pro
85 90 95

ACT TGG GGT GAC ACG GTT GAA GTG AAT ACT TGG GTT GCC AAG TCA GGG 816
Thr Trp Gly Asp Thr Val Glu Val Asn Thr Trp Val Ala Lys Ser Gly
100 105 110

AAA AAT GGT ATG CGT CGT GAC TGG CTC ATA AGT GAT TGT AAT ACT GGA 864
Lys Asn Gly Met Arg Arg Asp Trp Leu Ile Ser Asp Cys Asn Thr Gly
115 120 125

GAG ATT CTT ACA AGA GCA TCA AGC GTG TGG GTC ATG ATG AAT CAA AAG 912
Glu Ile Leu Thr Arg Ala Ser Ser Val Trp Val Met Met Asn Gln Lys
130 135 140 145

ACA AGA AGA TTG TCA AAA ATT CCA GAT GAG GTT CGA AAT GAG ATA GAG 960
Thr Arg Arg Leu Ser Lys Ile Pro Asp Glu Val Arg Asn Glu Ile Glu
150 155 160

CCT CAT TTT GTG GAC TCT CCT CCC GTC ATT GAA GAT GAT GAC CGG AAA 1008
Pro His Phe Val Asp Ser Pro Pro Val Ile Glu Asp Asp Asp Arg Lys
165 170 175

CTT CCC AAG CTG GAT GAG AAG ACT GCT GAC TCC ATC CGC AAG GGT CTA 1056
Leu Pro Lys Leu Asp Glu Lys Thr Ala Asp Ser Ile Arg Lys Gly Leu
180 185 190

ACT CCG AGG TGG AAT GAC TTG GAT GTC AAT CAG CAC GTC AAC AAC GTG 1104
Thr Pro Arg Trp Asn Asp Leu Asp Val Asn Gln His Val Asn Asn Val
195 200 205

AAG TAC ATC GGG TGG ATT CTT GAG AGT ACT CCA CCA GAA GTT CTG GAG 1152
Lys Tyr Ile Gly Trp Ile Leu Glu Ser Thr Pro Pro Glu Val Leu Glu
210 215 220 225

ACA CAG GAG TTA TGT TCC CTT ACC CTG GAA TAC AGG CGG GAA TGT GGA 1200
Thr Gln Glu Leu Cys Ser Leu Thr Leu Glu Tyr Arg Arg Glu Cys Gly
230 235 240

AAG GAG AGT GTT CTG GAG TCC CTC ACT GCT ATG GAC CCC TCT GGA GGG 1248
Lys Glu Ser Val Leu Glu Ser Leu Thr Ala Met Asp Pro Ser Gly Gly
245 250 255

GGC TAT GGG TCC CAG TTT CAG CAC CTT CTG CGG CTT GAG GAT GGA GGT 1296
Gly Tyr Gly Ser Gln Phe Gln His Leu Leu Arg Leu Glu Asp Gly Gly
260 265 270

GAG ATC GTG AAG GGG AGA ACC GAG TGG CGA ACC CAA GAA TGG TGT AAT 1344
Glu Ile Val Lys Gly Arg Thr Glu Trp Arg Thr Gln Glu Trp Cys Asn
275 280 285

CAA TGG GGT GGT ACC AAC CGG GGA GTC CTC GCC TGG AGA CTA CTC TTA 1392
Gln Trp Gly Gly Thr Asn Arg Gly Val Leu Ala Trp Arg Leu Leu Leu
290 395 300 305

GAA GGG GGA GCC CTG ACC CCT TTG GAG TTA TGC TTT CTT TAT TGT CGG 1440
Glu Gly Gly Ala Leu Thr Pro Leu Glu Leu Cys Phe Leu Tyr Cys Arg
310 315 320

ACG AGC TGAGTGAAGG GCAGGTAAGA TAGTAGCAAT CGGTAGATTG TGTAGTTTGT 1496
Thr Ser

TTGCTGCTTT TCACGATGGC TCTCGTGTAT AATATCATGG TCGTCTTCTT TGTATCCTCT 1556

TCGCATGTTC CGGGTTGATT TATACATTAT ATTCTTTCTA AAAAA 1601

( 2 ) INFORMATION FOR SEQ ID NO:7:

( i ) SEQUENCE CHARACTERISTICS:

( A ) LENGTH: 1744 base pairs ( B ) TYPE: nucleic acid ( C ) STRANDEDNESS: double -continued ( D ) TOPOLOGY: linear ( i i ) MOLECULE TYPE: cDNA to mRNA ( x i ) SEQUENCE DESCRIPTION: SEQ ID NO:7:

```
CTTTGATCGG TCGATCCTTT CCTCTCGCTC ATAATTTACC CATTAGTCCC CTTTGCCTTC    60

TTTAAACCCT CCTTTCCTTT CTCTTCCCTT CTTCCTCTCT GGGAAGTTTA AAGCTTTTGC   120

CTTTCTCCCC CCCACAACCT CTTTCCCGCA TTTGTTGAGC TGTTTTTTTG TCGCCATTCG   180

TCCTCTCCTC TTCAGTTCAA CAGAA ATG GTG GCT ACC GCT GCA AGT TCT GCA     232
                            Met Val Ala Thr Ala Ala Ser Ser Ala
                             1               5

TTC TTC CCC CTC CCA TCC GCC GAC ACC TCA TCG AGA CCC GGA AAG CTC     280
Phe Phe Pro Leu Pro Ser Ala Asp Thr Ser Ser Arg Pro Gly Lys Leu
 10                  15                  20                  25

GGC AAT AAG CCA TCG AGC TTG AGC CCC CTC AAG CCC AAA TCG ACC CCC     328
Gly Asn Lys Pro Ser Ser Leu Ser Pro Leu Lys Pro Lys Ser Thr Pro
                 30                  35                  40

AAT GGC GGT TTG CAG GTT AAG GCA AAT GCC AGT GCC CCT CCT AAG ATC     376
Asn Gly Gly Leu Gln Val Lys Ala Asn Ala Ser Ala Pro Pro Lys Ile
             45                  50                  55

AAT GGT TCC CCG GTC GGT CTA AAG TCG GGC GGT CTC AAG ACT CAG GAA     424
Asn Gly Ser Pro Val Gly Leu Lys Ser Gly Gly Leu Lys Thr Gln Glu
         60                  65                  70

GAC GCT CAT TCG GCC CCT CCT CCG CGA ACT TTT ATC AAC CAG TTG CCT     472
Asp Ala His Ser Ala Pro Pro Pro Arg Thr Phe Ile Asn Gln Leu Pro
     75                  80                  85

GAT TGG AGT ATG CTT CTT GCT GCA ATC ACG ACT GTC TTC TTG GCT GCA     520
Asp Trp Ser Met Leu Leu Ala Ala Ile Thr Thr Val Phe Leu Ala Ala
 90                  95                 100                 105

GAG AAG CAA TGG ATG ATG CTT GAT TGG AAA CCT AAG AGG CCT GAC ATG     568
Glu Lys Gln Trp Met Met Leu Asp Trp Lys Pro Lys Arg Pro Asp Met
                110                 115                 120

CTT GTG GAC CCG TTT GGA TTG GGA AGT ATT GTT CAG GAT GGG CTT GTG     616
Leu Val Asp Pro Phe Gly Leu Gly Ser Ile Val Gln Asp Gly Leu Val
            125                 130                 135

TTC AGG CAG AAT TTT TCG ATT AGG TCC TAT GAA ATA GGC GCC GAT CGC     664
Phe Arg Gln Asn Phe Ser Ile Arg Ser Tyr Glu Ile Gly Ala Asp Arg
        140                 145                 150

ACT GCG TCT ATA GAG ACG GTG ATG AAC CAT TTG CAG GAA ACA GCT CTC     712
Thr Ala Ser Ile Glu Thr Val Met Asn His Leu Gln Glu Thr Ala Leu
    155                 160                 165

AAT CAT GTT AAG ATT GCT GGG CTT TCT AAT GAC GGC TTT GGT CGT ACT     760
Asn His Val Lys Ile Ala Gly Leu Ser Asn Asp Gly Phe Gly Arg Thr
170                 175                 180                 185

CCT GAG ATG TAT AAA AGG GAC CTT ATT TGG GTT GTT GCG AAA ATG CAA     808
Pro Glu Met Tyr Lys Arg Asp Leu Ile Trp Val Val Ala Lys Met Gln
                190                 195                 200

GTC ATG GTT AAC CGC TAT CCT ACT TGG GGT GAC ACG GTT GAA GTG AAT     856
Val Met Val Asn Arg Tyr Pro Thr Trp Gly Asp Thr Val Glu Val Asn
            205                 210                 215

ACT TGG GTT GCC AAG TCA GGG AAA AAT GGT ATG CGT CGT GAC TGG CTC     904
Thr Trp Val Ala Lys Ser Gly Lys Asn Gly Met Arg Arg Asp Trp Leu
        220                 225                 230

ATA AGT GAT TGC AAT ACT GGA GAG ATT CTT ACA AGA GCA TCA AGC GTG     952
Ile Ser Asp Cys Asn Thr Gly Glu Ile Leu Thr Arg Ala Ser Ser Val
    235                 240                 245

TGG GTC ATG ATG AAT CAA AAG ACA AGA AGA TTG TCA AAA ATT CCA GAT    1000
Trp Val Met Met Asn Gln Lys Thr Arg Arg Leu Ser Lys Ile Pro Asp
250                 255                 260                 265
```

-continued

GAG GTT CGA AAT GAG ATA GAG CCT CAT TTT GTG GAC TCT CCT CCC GTC 1048
Glu Val Arg Asn Glu Ile Glu Pro His Phe Val Asp Ser Pro Pro Val
270 275 280

ATT GAA GAC GAT GAC CGG AAA CTT CCC AAG CTG GAT GAG AAG ACT GCT 1096
Ile Glu Asp Asp Asp Arg Lys Leu Pro Lys Leu Asp Glu Lys Thr Ala
285 290 295

GAC TCC ATC CGC AAG GGT CTA ACT CCG AGG TGG AAT GAC TTG GAT GTC 1144
Asp Ser Ile Arg Lys Gly Leu Thr Pro Arg Trp Asn Asp Leu Asp Val
300 305 310

AAT CAA CAC GTC AAC AAC GTG AAG TAC ATC GGG TGG ATT CTT GAG AGT 1192
Asn Gln His Val Asn Asn Val Lys Tyr Ile Gly Trp Ile Leu Glu Ser
315 320 325

ACT CCA CCA GAA GTT CTG GAG ACC CAG GAG TTA TGT TCC CTT ACT CTG 1240
Thr Pro Pro Glu Val Leu Glu Thr Gln Glu Leu Cys Ser Leu Thr Leu
330 335 340 345

GAA TAC AGG CGG GAA TGT GGA AGG GAG AGC GTG CTG GAG TCC CTC ACT 1288
Glu Tyr Arg Arg Glu Cys Gly Arg Glu Ser Val Leu Glu Ser Leu Thr
350 355 360

GCT ATG GAT CCC TCT GGA GGG GGT TAT GGG TCC CAG TTT CAG CAC CTT 1336
Ala Met Asp Pro Ser Gly Gly Gly Tyr Gly Ser Gln Phe Gln His Leu
365 370 375

CTG CGG CTT GAG GAT GGA GGT GAG ATC GTG AAG GGG AGA ACT GAG TGG 1384
Leu Arg Leu Glu Asp Gly Gly Glu Ile Val Lys Gly Arg Thr Glu Trp
380 385 390

CGG CCC AAG AAT GGT GTA ATC AAT GGG GTG GTA CCA ACC GGG GAG TCC 1432
Arg Pro Lys Asn Gly Val Ile Asn Gly Val Val Pro Thr Gly Glu Ser
395 400 405

TCA CCT GGA GAC TAC TCT TAGAAGGGAG CCCTGACCCC TTTGGAGTTG 1480
Ser Pro Gly Asp Tyr Ser
410 415

TGATTTCTTT ATTGTCGGAC GAGCTAAGTG AAGGGCAGGT AAGATAGTAG CAATCGGTAG 1540

ATTGTGTAGT TTGTTTGCTG CTTTTTCACG ATGGCTCTCG TGTATAATAT CATGGTCTGT 1600

CTTCTTTGTA TCCTCTTCTT CGCATGTTCC GGGTTGATTC ATACATTATA TTCTTTCTAT 1660

TTGTTTGAAG GCGAGTAGCG GGTTGTAATT ATTTATTTTG TCATTACAAT GTCGTTTAAC 1720

TTTTCAAATG AAACTACTTA TGTG 1744

( 2 ) INFORMATION FOR SEQ ID NO:8:

( i ) SEQUENCE CHARACTERISTICS:
( A ) LENGTH: 1474 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:8:

CTGGATACCA TTTTCCCTGC GAAAAAAC ATG GTG GCT GCT GCA GCA AGT TCC 52
Met Val Ala Ala Ala Ala Ser Ser
1 5

GCA TTC TTC CCT GTT CCA GCC CCG GGA GCC TCC CCT AAA CCC GGG AAG 100
Ala Phe Phe Pro Val Pro Ala Pro Gly Ala Ser Pro Lys Pro Gly Lys
10 15 20

TTC GGA AAT TGG CCC TCG AGC TTG AGC CCT TCC TTC AAG CCC AAG TCA 148
Phe Gly Asn Trp Pro Ser Ser Leu Ser Pro Ser Phe Lys Pro Lys Ser
25 30 35 40

ATC CCC AAT GGC GGA TTT CAG GTT AAG GCA AAT GAC AGC GCC CAT CCA 196
Ile Pro Asn Gly Gly Phe Gln Val Lys Ala Asn Asp Ser Ala His Pro
45 50 55

AAG GCT AAC GGT TCT GCA GTT AGT CTA AAG TCT GGC AGC CTC AAC ACT 244

-continued

```
Lys Ala Asn Gly Ser Ala Val Ser Leu Lys Ser Gly Ser Leu Asn Thr
             60                  65                  70

CAG GAG GAC ACT TCG TCG TCC CCT CCT CCT CGG ACT TTC CTT CAC CAG    292
Gln Glu Asp Thr Ser Ser Ser Pro Pro Pro Arg Thr Phe Leu His Gln
         75                  80                  85

TTG CCT GAT TGG AGT AGG CTT CTG ACT GCA ATC ACG ACC GTG TTC GTG    340
Leu Pro Asp Trp Ser Arg Leu Leu Thr Ala Ile Thr Thr Val Phe Val
     90                  95                 100

AAA TCT AAG AGG CCT GAC ATG CAT GAT CGG AAA TCC AAG AGG CCT GAC    388
Lys Ser Lys Arg Pro Asp Met His Asp Arg Lys Ser Lys Arg Pro Asp
105                 110                 115                 120

ATG CTG GTG GAC TCG TTT GGG TTG GAG AGT ACT GTT CAG GAT GGG CTC    436
Met Leu Val Asp Ser Phe Gly Leu Glu Ser Thr Val Gln Asp Gly Leu
                125                 130                 135

GTG TTC CGA CAG AGT TTT TCG ATT AGG TCT TAT GAA ATA GGC ACT GAT    484
Val Phe Arg Gln Ser Phe Ser Ile Arg Ser Tyr Glu Ile Gly Thr Asp
            140                 145                 150

CGA ACG GCC TCT ATA GAG ACA CTT ATG AAC CAC TTG CAG GAA ACA TCT    532
Arg Thr Ala Ser Ile Glu Thr Leu Met Asn His Leu Gln Glu Thr Ser
        155                 160                 165

CTC AAT CAT TGT AAG AGT ACC GGT ATT CTC CTT GAC GGC TTC GGT CGT    580
Leu Asn His Cys Lys Ser Thr Gly Ile Leu Leu Asp Gly Phe Gly Arg
    170                 175                 180

ACT CTT GAG ATG TGT AAA AGG GAC CTC ATT TGG GTG GTA ATA AAA ATG    628
Thr Leu Glu Met Cys Lys Arg Asp Leu Ile Trp Val Val Ile Lys Met
185                 190                 195                 200

CAG ATC AAG GTG AAT CGC TAT CCA GCT TGG GGC GAT ACT GTC GAG ATC    676
Gln Ile Lys Val Asn Arg Tyr Pro Ala Trp Gly Asp Thr Val Glu Ile
                205                 210                 215

AAT ACC CGG TTC TCC CGG TTG GGG AAA ATC GGT ATG GGT CGC GAT TGG    724
Asn Thr Arg Phe Ser Arg Leu Gly Lys Ile Gly Met Gly Arg Asp Trp
            220                 225                 230

CTA ATA AGT GAT TGC AAC ACA GGA GAA ATT CTT GTA AGA GCT ACG AGC    772
Leu Ile Ser Asp Cys Asn Thr Gly Glu Ile Leu Val Arg Ala Thr Ser
        235                 240                 245

GCG TAT GCC ATG ATG AAT CAA AAG ACG AGA AGA CTC TCA AAA CTT CCA    820
Ala Tyr Ala Met Met Asn Gln Lys Thr Arg Arg Leu Ser Lys Leu Pro
    250                 255                 260

TAC GAG GTT CAC CAG GAG ATA GTG CCT CTT TTT GTC GAC TCT CCT GTC    868
Tyr Glu Val His Gln Glu Ile Val Pro Leu Phe Val Asp Ser Pro Val
265                 270                 275                 280

ATT GAA GAC AGT GAT CTG AAA GTG CAT AAG TTT AAA GTG AAG ACT GGT    916
Ile Glu Asp Ser Asp Leu Lys Val His Lys Phe Lys Val Lys Thr Gly
                285                 290                 295

GAT TCC ATT CAA AAG GGT CTA ACT CCG GGG TGG AAT GAC TTG GAT GTC    964
Asp Ser Ile Gln Lys Gly Leu Thr Pro Gly Trp Asn Asp Leu Asp Val
            300                 305                 310

AAT CAG CAC GTA AGC AAC GTG AAG TAC ATT GGG TGG ATT CTC GAG AGT   1012
Asn Gln His Val Ser Asn Val Lys Tyr Ile Gly Trp Ile Leu Glu Ser
        315                 320                 325

ATG CCA ACA GAA GTT TTG GAG ACC CAG GAG CTA TGC TCT CTC GCC CTT   1060
Met Pro Thr Glu Val Leu Glu Thr Gln Glu Leu Cys Ser Leu Ala Leu
    330                 335                 340

GAA TAT AGG CGG GAA TGC GGA AGG GAC AGT GTG CTG GAG TCC GTG ACC   1108
Glu Tyr Arg Arg Glu Cys Gly Arg Asp Ser Val Leu Glu Ser Val Thr
345                 350                 355                 360

GCT ATG GAT CCC TCA AAA GTT GGA GTC CGT TCT CAG TAC CAG CAC CTT   1156
Ala Met Asp Pro Ser Lys Val Gly Val Arg Ser Gln Tyr Gln His Leu
                365                 370                 375

CTG CGG CTT GAG GAT GGG ACT GCT ATC GTG AAC GGT GCA ACT GAG TGG   1204
```

-continued

```
Leu Arg Leu Glu Asp Gly Thr Ala Ile Val Asn Gly Ala Thr Glu Trp
            380                 385                 390

CGG CCG AAG AAT GCA GGA GCT AAC GGG GCG ATA TCA ACG GGA AAG ACT    1252
Arg Pro Lys Asn Ala Gly Ala Asn Gly Ala Ile Ser Thr Gly Lys Thr
        395                 400                 405

TCA AAT GGA AAC TCG GTC TCT TAGAAGTGTC TCGGAACCCT TCCGAGATGT       1303
Ser Asn Gly Asn Ser Val Ser
    410                 415

GCATTTCTTT TCTCCTTTTC ATTTTGTGGT GAGCTGAAAG AAGAGCATGT CGTTGCAATC 1363

AGTAAATTGT GTAGTTCGTT TTTCGCTTTG CTTCGCTCCT TTGTATAATA ATATGGTCAG 1423

TCGTCTTTGT ATCATTTCAT GTTTTCAGTT TATTTACGCC ATATAATTTT T          1474
```

( 2 ) INFORMATION FOR SEQ ID NO:9:

( i ) SEQUENCE CHARACTERISTICS:
( A ) LENGTH: 976 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:9:

```
GGCACGAGAA ACATGGTGGC TGCCGCAGCA AGTTCTGCAT TCTTCTCCGT TCCAACCCCG   60

GGAATCTCCC CTAAACCCGG GAAGTTCGGT AATGGTGGCT TTCAGGTTAA GGCAAACGCC  120

AATGCCCATC CTAGTCTAAA GTCTGGCAGC CTCGAGACTG AAGATGACAC TTCATCGTCG  180

TCCCCTCCTC CTCGGACTTT CATTAACCAG TTGCCCGACT GGAGTATGCT TCTGTCCGCA  240

ATCACGACTA TCTTCGGGGC AGCTGAGAAG CAGTGGATGA TGCTTGATAG GAAATCTAAG  300

NAGACCCGAC ATGCTCATGG CAACCGTTTG GGGTTGACAG TATTGTTCAG GATGGGGTTT  360

TTTTCAGACA GAGTTTTTCG ATTAGATCTT ACGAAATAGG CGCTGATCGA ACAACCTCAA  420

TAGAGACGCT GATGAACATG TTCCAGGAAA CGTCTTTGAA TCATTGTAAG AGTAACGGTC  480

TTCTCAATGA CGGCTTTGGT CGCACTCCTG AGATGTGTAA GAAGGGCCTC ATTTGGGTGG  540

TTACGAAAAT GCAGGTCGAG GTGAATCGCT ATCCTATTTG GSGTGATTCT ATCGAAGTCA  600

ATACTTGGGT CTCCGAGTCG GGGNAAAANC GGTATGGGTC GTGATTGGCT GATAAGTGAT  660

TGCAGTACAG GAGNAAATTC TTGTAAGAGC AACGAGCGTG TGGGCTATGA TGAATCAAAA  720

GACGAGAAGA TTGTCAAAAT TTCCATTTGA GGTTCGACAA GAGATAGCGC CTAATTTTGT  780

CGACTCTGTT CCTGTCATTG AAGACGATCG AAAATTACAC AAGCTTGATG TGAAGACGGG  840

TGATTCCATT CACAATGGTC TAACTCCAAG GTGGAATGAC TTGGATGTCA ATCAGCACGT  900

TAACAATGTG AAATACATTG GGTGGATTCT CAAGAGTGTT CCAACAGATG TTTTTGGGGC  960

CCAGGAGCTA TGTGGA                                                  976
```

( 2 ) INFORMATION FOR SEQ ID NO:10:

( i ) SEQUENCE CHARACTERISTICS:
( A ) LENGTH: 1670 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:10:

```
GAATTCGGCA CGAGTCTCTC TCTCTCTCTC TCTCTCTCTC TCTCTCTCTC TCTCTCTCTC   60

TCTCCCCAAC GAAATTTCAA TTCCATTAGC TGTTGACAAA AACAGCTGAA GATCACAAAT  120
```

-continued

```
TTGTTCTCAG AGGAAGAAAA GGAAGGAAGG AAGGAAGGAG GAGGAAGCCA TTGTGGGCAA  180
TATTTGATCG GTGGATCCTT TCCTCCCGCT CGTTGAAAGA CAATGGTGGC TACCGCTGCA  240
AGCTCTGCAT TCTTCCCCGT GTCGTCCCCG GTCACCTCCT CTAGACCAGG AAAGCCCGGA  300
AATGGGTCAT CGAGCTTCAG CCCCATCAAG CCCAAATTTG TCGCCAATGG CGGGTTGCAG  360
GTTAAGGCAA ACGCCAGTGC CCCTCCTAAG ATCAATGGTT CCTCGGTCGG TCTAAAGTCC  420
TGCAGTCTCA AGACTCAGGA AGACACTCCT TCGGCCCCTG CTCCACGGAC TTTTATCAAC  480
CAGTTGCCTG ATTGGAGTAT GCTTCTTGCT GCAATTACTA CTGTCTTCTT GGCAGCAGAG  540
AAGCAGTGGA TGATGCTTGA TTGGAAACCT AAGAGGCCTG ACATGCTTGT GGACCCGTTC  600
GGATTGGGAA GTATTGTCCA GCATGGGCTT GTGTTCAGGC AGAATTTTTC GATTAGGTCC  660
TATGAAATAG GCGCTGATCG CACTGCGTCT ATAGAGACGG TGATGAACCA CTTGCAGGAA  720
ACGGCTCTCA ATCATGTTAA GAGTGCGGGG CTTATGAATG ACGGCTTTGG TCGTACTCCT  780
GAGATGTATA AAAAGGACCT TATTTGGGTT GTCGCGAAAA TGCAGGTCAT GGTTAACCGC  840
TATCCTACTT GGGGTGACAC AGTTGAAGTG AATACTTGGG TTGCCAAGTC AGGGAAAAAT  900
GGTATGCGTC GTGATTGGCT CATAAGTGAT TGTAATACAG GAGAAATTCT TACTAGAGCA  960
TCAAGCGTGT GGGTCATGAT GAATCAAAAG ACAAGAAGAT TGTCAAAAAT TCCAGATGAG 1020
GTTCGGCATG AGATTGAGCC TCATTTTGTG GACTCTCCTC CCGTCATTGA AGACGATGAC 1080
CGAAAACTTC CCAAGCTGGA TGACAAGACT GCTGACTCCA TCCGCAAGGG TCTAACTCCG 1140
AAGTGGAATG ACTTGGATGT CAATCAGCAC GTCAACAACG TGAAGTACAT CGGGTGGATT 1200
CTTGAGAGTA CTCCACAAGA AGTTCTGGAG ACCCAGGAGC TATGTTCCCT TACCCTGGAA 1260
TACAGGCGGG AATGCGGAAG GGAGAGCGTG CTGGAGTCCC TCACTGCTGC GGACCCCTCT 1320
GGAAAGGGCT TTGGGTCCCA GTTCCAGCAC CTTCTGAGGC TTGAGGATGG AGGGGAGATT 1380
GTGAAGGGGA GAACTGAGTG GCGACCAAAG ACTGCAGGTA TCAATGGGGC GATACCATCC 1440
GGGGAGACCT CACCTGGAGA CTCTTAGAAG GGAGCCCTGG TCCCTTTGGA GTTCTGCTTT 1500
CTTTATGGTC GGATGAGCTG AGTGAACTGC AGGTAAGGTA GTAGCAATCG GTAGATTGTT 1560
TAGTTTGTTT GCTGTTTTTT ACTCCGGCTC TCTTTTATAA TGTCATGGTC TCATTTGTAT 1620
CCTCACATGT TTCGGGTTGA TTTATACAAT ATATTATTTC TATTTGTTTC            1670
```

( 2 ) INFORMATION FOR SEQ ID NO:11:

( i ) SEQUENCE CHARACTERISTICS:
( A ) LENGTH: 1310 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:11:

```
GGCACGAGTG CCTCTTCTCC ATCTCGTCCT CCCCACATAC TGAGCCACCC AGAGAGAGAA   60

CCCAGCCGCT GTTCCCTCGG AA ATG TTG AAG CTT TCT TGC AAT GCC GCC ACC   112
                         Met Leu Lys Leu Ser Cys Asn Ala Ala Thr
                          1               5                  10

GAC CAG ATT CTG TCG TCG GCC GTG GCT CAA ACC GCA TTA TGG GGT CAA   160
Asp Gln Ile Leu Ser Ser Ala Val Ala Gln Thr Ala Leu Trp Gly Gln
                15                  20                  25

CCC AGA AAC AGA TCC TTT TCA ATG TCC GCC CGG AGA AGG GGA GCC GTT   208
Pro Arg Asn Arg Ser Phe Ser Met Ser Ala Arg Arg Arg Gly Ala Val
            30                  35                  40
```

-continued

TGC TGC GCG CCT CCA GCT GCT GGA AAG CCC CCT GCC ATG ACC GCT GTT 256
Cys Cys Ala Pro Pro Ala Ala Gly Lys Pro Pro Ala Met Thr Ala Val
45 50 55

ATC CCA AAA GAC GGG GTG GCC TCG TCC GGG TCC GGC AGC CTG GCC GAC 304
Ile Pro Lys Asp Gly Val Ala Ser Ser Gly Ser Gly Ser Leu Ala Asp
60 65 70

CAG CTG AGG CTC GGG AGC CGT ACG CAG AAT GGG CTG TCG TAC ACG GAG 352
Gln Leu Arg Leu Gly Ser Arg Thr Gln Asn Gly Leu Ser Tyr Thr Glu
75 80 85 90

AAG TTC ATT GTC AGG TGC TAC GAG GTC GGT ATT AAC AAG ACA GCC ACT 400
Lys Phe Ile Val Arg Cys Tyr Glu Val Gly Ile Asn Lys Thr Ala Thr
95 100 105

GTC GAA ACC ATG GCC AAT CTC TTG CAG GAA GTA GGT TGT AAC CAT GCT 448
Val Glu Thr Met Ala Asn Leu Leu Gln Glu Val Gly Cys Asn His Ala
110 115 120

CAG AGT GTT GGA TTC TCA ACT GAC GGG TTT GCG ACG ACG CCT ACC ATG 496
Gln Ser Val Gly Phe Ser Thr Asp Gly Phe Ala Thr Thr Pro Thr Met
125 130 135

AGG AAA TTG AAT CTG ATA TGG GTT ACT GCT CGA ATG CAC ATA GAA ATT 544
Arg Lys Leu Asn Leu Ile Trp Val Thr Ala Arg Met His Ile Glu Ile
140 145 150

TAT AAG TAC CCA GCA TGG AGT GAT GTG GTT GAA ATC GAG ACT TGG TGC 592
Tyr Lys Tyr Pro Ala Trp Ser Asp Val Val Glu Ile Glu Thr Trp Cys
155 160 165 170

CAA AGT GAA GGA AGA ATC GGA ACA AGA AGG GAT TGG ATT CTC AAG GAT 640
Gln Ser Glu Gly Arg Ile Gly Thr Arg Arg Asp Trp Ile Leu Lys Asp
175 180 185

TAT GGT AAT GGT GAA GTT ATT GGA AGA GCC ACA AGC AAG TGG GTG ATG 688
Tyr Gly Asn Gly Glu Val Ile Gly Arg Ala Thr Ser Lys Trp Val Met
190 195 200

ATG AAC CAG AAC ACT AGA CGA CTC CAA AAA GTT GAT GAT TCC GTT CGA 736
Met Asn Gln Asn Thr Arg Arg Leu Gln Lys Val Asp Asp Ser Val Arg
205 210 215

GAA GAG TAT ATG GTT TTC TGT CCA CGC GAA CCA AGG TTA TCA TTT CCT 784
Glu Glu Tyr Met Val Phe Cys Pro Arg Glu Pro Arg Leu Ser Phe Pro
220 225 230

GAA GAG AAC AAT CGG AGT TTG AGA AAA ATA TCT AAA TTG GAA GAT CCT 832
Glu Glu Asn Asn Arg Ser Leu Arg Lys Ile Ser Lys Leu Glu Asp Pro
235 240 245 250

GCT GAG TAT TCG AGA CTT GGT CTT ACG CCT AGA AGA GCT GAT CTG GAT 880
Ala Glu Tyr Ser Arg Leu Gly Leu Thr Pro Arg Arg Ala Asp Leu Asp
255 260 265

ATG AAC CAG CAT GTC AAC AAC GTT GCT TAC ATA GGT TGG GCT CTG GAG 928
Met Asn Gln His Val Asn Asn Val Ala Tyr Ile Gly Trp Ala Leu Glu
270 275 280

AGT GTA CCT CAA GAA ATA ATC GAC TCT TAT GAG CTG GAA ACT ATC ACT 976
Ser Val Pro Gln Glu Ile Ile Asp Ser Tyr Glu Leu Glu Thr Ile Thr
285 290 295

CTG GAC TAC AGA AGA GAA TGC CAA CAG GAT GAC GTA GTC GAT TCG CTC 1024
Leu Asp Tyr Arg Arg Glu Cys Gln Gln Asp Asp Val Val Asp Ser Leu
300 305 310

ACC AGT GTT CTG TCA GAT GAG GAA TCA GGA ACA TTA CCA GAG CTC AAG 1072
Thr Ser Val Leu Ser Asp Glu Glu Ser Gly Thr Leu Pro Glu Leu Lys
315 320 325 330

GGA ACA AAT GGA TCT GCA TCC ACC CCA CTG AAA CGT GAC CAT GAT GGC 1120
Gly Thr Asn Gly Ser Ala Ser Thr Pro Leu Lys Arg Asp His Asp Gly
335 340 345

TCT CGC CAG TTC TTG CAC TTG CTG AGG CTC TCC CCC GAC GGG CTA GAA 1168
Ser Arg Gln Phe Leu His Leu Leu Arg Leu Ser Pro Asp Gly Leu Glu
350 355 360

-continued

ATA AAC CGT GGC CGA ACT GAA TGG AGA AAG AAA TCC ACG AAA 1210
Ile Asn Arg Gly Arg Thr Glu Trp Arg Lys Lys Ser Thr Lys
365 370 375

TAGAGGAGTC TCTTACATCC TGCCCATCTG GTTTGATCTG CATATGGTAT TTTCCCTTGC 1270

ACGCTTTTGC TTCCTGTTTA TTTGAGTTTG ATTCAGCACC 1310

( 2 ) INFORMATION FOR SEQ ID NO:12:

( i ) SEQUENCE CHARACTERISTICS:
( A ) LENGTH: 1307 base pairs
( B ) TYPE: nucleic acid
( C ) STRANDEDNESS: double
( D ) TOPOLOGY: linear ( i i ) MOLECULE TYPE: cDNA to mRNA ( x i ) SEQUENCE DESCRIPTION: SEQ ID NO:12:

GCTCGCCTCC CACATTTTCT TCTTCGATCC CGAAAAG ATG TTG AAG CTC TCG TGT 55
Met Leu Lys Leu Ser Cys
1 5

AAT GCG ACT GAT AAG TTA CAG ACC CTC TTC TCG CAT TCT CAT CAA CCG 103
Asn Ala Thr Asp Lys Leu Gln Thr Leu Phe Ser His Ser His Gln Pro
10 15 20

GAT CCG GCA CAC CGG AGA ACC GTC TCC TCC GTG TCG TGC TCT CAT CTG 151
Asp Pro Ala His Arg Arg Thr Val Ser Ser Val Ser Cys Ser His Leu
25 30 35

AGG AAA CCG GTT CTC GAT CCT TTG CGA GCG ATC GTA TCT GCT GAT CAA 199
Arg Lys Pro Val Leu Asp Pro Leu Arg Ala Ile Val Ser Ala Asp Gln
40 45 50

GGA AGT GTG ATT CGA GCA GAA CAA GGT TTG GGC TCA CTC GCG GAT CAG 247
Gly Ser Val Ile Arg Ala Glu Gln Gly Leu Gly Ser Leu Ala Asp Gln
55 60 65 70

CTC CGA TTG GGT AGC TTG ACG GAG GAT GGT TTG TCG TAT AAG GAG AAG 295
Leu Arg Leu Gly Ser Leu Thr Glu Asp Gly Leu Ser Tyr Lys Glu Lys
75 80 85

TTC ATC GTC AGA TCC TAC GAA GTG GGG AGT AAC AAG ACC GCC ACT GTC 343
Phe Ile Val Arg Ser Tyr Glu Val Gly Ser Asn Lys Thr Ala Thr Val
90 95 100

GAA ACC GTC GCT AAT CTT TTG CAG GAG GTG GGA TGT AAT CAT GCG CAG 391
Glu Thr Val Ala Asn Leu Leu Gln Glu Val Gly Cys Asn His Ala Gln
105 110 115

AGC GTT GGA TTC TCG ACT GAT GGG TTT GCG ACA ACA CCG ACC ATG AGG 439
Ser Val Gly Phe Ser Thr Asp Gly Phe Ala Thr Thr Pro Thr Met Arg
120 125 130

AAA CTG CAT CTC ATT TGG GTC ACT GCG AGA ATG CAT ATA GAG ATC TAC 487
Lys Leu His Leu Ile Trp Val Thr Ala Arg Met His Ile Glu Ile Tyr
135 140 145 150

AAG TAC CCT GCT TGG GGT GAT GTG GTT GAG ATA GAG ACA TGG TGT CAG 535
Lys Tyr Pro Ala Trp Gly Asp Val Val Glu Ile Glu Thr Trp Cys Gln
155 160 165

AGT GAA GGA AGG ATC GGG ACT AGG CGT GAT TGG ATT CTT AAG GAT GTT 583
Ser Glu Gly Arg Ile Gly Thr Arg Arg Asp Trp Ile Leu Lys Asp Val
170 175 180

GCT ACG GGT GAA GTC ACT GGC CGT GCT ACA AGC AAG TGG GTG ATG ATG 631
Ala Thr Gly Glu Val Thr Gly Arg Ala Thr Ser Lys Trp Val Met Met
185 190 195

AAC CAA GAC ACA AGA CGG CTT CAG AAA GTT TCT GAT GAT GTT CGG GAC 679
Asn Gln Asp Thr Arg Arg Leu Gln Lys Val Ser Asp Asp Val Arg Asp
200 205 210

GAG TAC TTG GTC TTC TGT CCT AAA GAA CTC AGA TTA GCA TTT CCT GAG 727
Glu Tyr Leu Val Phe Cys Pro Lys Glu Leu Arg Leu Ala Phe Pro Glu
215 220 225 230

-continued

```
GAG AAT AAC AGA AGC TTG AAG AAA ATT CCG AAA CTC GAA GAT CCA GCT        775
Glu Asn Asn Arg Ser Leu Lys Lys Ile Pro Lys Leu Glu Asp Pro Ala
                235                 240                 245

CAG TAT TCG ATG ATT GGG CTT AAG CCT AGA CGA GCT GAT CTC GAC ATG        823
Gln Tyr Ser Met Ile Gly Leu Lys Pro Arg Arg Ala Asp Leu Asp Met
            250                 255                 260

AAC CAG CAT GTC AAT AAT GTC ACC TAT ATT GGA TGG GTT CTT GAG AGC        871
Asn Gln His Val Asn Asn Val Thr Tyr Ile Gly Trp Val Leu Glu Ser
        265                 270                 275

ATA CCT CAA GAG ATT GTA GAC ACG CAC GAA CTT CAG GTC ATA ACT CTG        919
Ile Pro Gln Glu Ile Val Asp Thr His Glu Leu Gln Val Ile Thr Leu
    280                 285                 290

GAT TAC AGA AGA GAA TGT CAA CAA GAC GAT GTG GTG GAT TCA CTC ACC        967
Asp Tyr Arg Arg Glu Cys Gln Gln Asp Asp Val Val Asp Ser Leu Thr
295                 300                 305                 310

ACT ACC ACC TCA GAG ATT GGT GGG ACC AAT GGC TCT GCA TCA TCA GGC       1015
Thr Thr Thr Ser Glu Ile Gly Gly Thr Asn Gly Ser Ala Ser Ser Gly
                315                 320                 325

ACA CAG GGG CAA AAC GAT AGC CAG TTC TTA CAT CTC TTA AGG CTG TCT       1063
Thr Gln Gly Gln Asn Asp Ser Gln Phe Leu His Leu Leu Arg Leu Ser
            330                 335                 340

GGA GAC GGT CAG GAG ATC AAC CGC GGG ACA ACC CTG TGG AGA AAG AAG       1111
Gly Asp Gly Gln Glu Ile Asn Arg Gly Thr Thr Leu Trp Arg Lys Lys
        345                 350                 355

CCC TCC AAT CTC TAAGCCATTT CGTTCTTAAG TTTCCTCTAT CTGTGTCGCT          1163
Pro Ser Asn Leu
    360

CGATGCTTCA CGAGTCTAGT CAGGTCTCAT TTTTTTCAAT CTAAATTTGG GTTAGACTAG     1223

AGAACTGGAA TTATTGGAAT TTATGAGTTT TCGTTCTTGT TTCTGTACAA ATCTTGAGGA     1283

TTGAAGCCAA ACCCATTTCA TCTT                                            1307
```

( 2 ) INFORMATION FOR SEQ ID NO:13:

( i ) SEQUENCE CHARACTERISTICS:
( A ) LENGTH: 100 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: synthetic oligonucleotides ( x i ) SEQUENCE DESCRIPTION: SEQ ID NO:13:

```
CGGTCTAGAT AACAATCAAT GCAAGACTAT TGCACACGTG TTGCGTGTGA ACAATGGTCA     60

GGAGCTTCAC GTCTGGGAAA CGCCCCCAAA AGAAAACGTG                          100
```

( 2 ) INFORMATION FOR SEQ ID NO:14:

( i ) SEQUENCE CHARACTERISTICS:
( A ) LENGTH: 100 base pairs
( B ) TYPE: nucleic acid
( C ) STRANDEDNESS: single
( D ) TOPOLOGY: linear ( i i ) MOLECULE TYPE: synthetic oligonucleotides ( x i ) SEQUENCE DESCRIPTION: SEQ ID NO:14:

```
ATACTCGGCC AATCCAGCGA AGTGGTCCAT TCTTCTGGCG AAACCAGAAG CAATCAAAAT     60

GGTGTTGTTT TTAAAAGGCA CGTTTTCTTT TGGGGGCGTT                          100
```

C8 AND C10 MEDIUM-CHAIN THIOESTERASES IN PLANTS

This application is a continuation-in-part of U.S. Ser. No. 07/968,971 filed Oct. 30, 1992 now U.S. Pat. No. 5,455,167.

TECHNICAL FIELD

The present invention is directed to amino acid and nucleic acid sequences and constructs, and methods related thereto.

BACKGROUND

Members of several plant families synthesize large amount of predominantly medium-chain (C8–C14) triacylglycerols in specialized storage tissues, some of which are harvested for production of important dietary or industrial medium-chain fatty acids (F. D. Gunstone, *The Lipid Handbook* (Chapman & Hall, New York, 1986) pp. 55–112). Laurate (C12:0), for example, is currently extracted from seeds of tropical trees at a rate approaching one million tons annually (Battey, et al., *Tibtech* (1989) 71:122–125).

The mechanism by which the ubiquitous long-chain fatty acid synthesis is switched to specialized medium-chain production has been the subject of speculation for many years (Harwood, *Ann. Rev. Plant Physiol. Plant Mol. Biology* (1988) 39:101–138). Recently, Pollard, et al., (*Arch. of Biochem. and Biophys.* (1991) 284:1–7) identified a medium-chain acyl-ACP thioesterase activity in developing oilseeds of California bay, *Umbellularia californica*. This activity appears only when the developing cotyledons become committed to the near-exclusive production of triglycerides with lauroyl (12:0) and caproyl (10:0) fatty acids. This work presented the first evidence for a mechanism for medium-chain fatty acid synthesis in plants: During elongation the fatty acids remain esterified to acyl-carrier protein (ACP). If the thioester is hydrolized prematurely, elongation is terminated by release of the medium-chain fatty acid. The Bay thioesterase was subsequently purified by Davies et al., (*Arch. Biochem. Biophys.* (1991) 290:37–45) which allowed the cloning of a corresponding cDNA which has been used to obtain related clones and to modify the triglyceride composition of plants (WO 91/16421 and WO 92/20236).

SUMMARY OF THE INVENTION

By this invention, further plant medium-chain thioesterases, and uses of plant long-chain thioesterase antisense sequences are provided. In addition, uses of medium-chain thioesterases from non-plant sources are considered.

In a first embodiment, this invention is directed to nucleic acid sequences which encode plant medium-chain preferring thioesterases, in particular those which demonstrate preferential activity towards fatty acyl-ACPs having a carbon chain length of C8 or C10. This includes sequences which encode biologically active plant thioesterases as well as sequences which are to be used as probes, vectors for transformation or cloning intermediates. Biologically active sequences are preferentially found in a sense orientation with respect to transcriptional regulatory regions found in various constructs. The plant thioesterase encoding sequences may encode a complete or partial sequence depending upon the intended use. The instant invention pertains to the entire or portions of the genomic sequence or cDNA sequence and to the thioesterase protein encoded thereby, including precursor or mature plant thioesterase. Plant thioesterases exemplified herein include a *Cuphea*

*hookeriana* (Cuphea) and an Ulmacea (elm) thioesterase. The exemplified thioesterase sequences may also be used to obtain other similar plant thioesterases.

Of special interest are recombinant DNA constructs which can provide for the transcription or transcription and translation (expression) of the plant thioesterase sequence. In particular, constructs which are capable of transcription or transcription and translation in plant host cells are preferred. Such construct may contain a variety of regulatory regions including transcriptional initiation regions obtained from genes preferentially expressed in plant seed tissue.

In a second aspect, this invention relates to the presence of such constructs in host cells, especially plant host cells, and to a method for producing a plant thioesterase in a host cell or progeny thereof via the expression of a construct in the cell. In a related aspect, this invention includes transgenic host cells which have an expressed plant thioesterase therein.

In a different embodiment, this invention relates to methods of using a DNA sequence encoding a plant thioesterase for the modification of the proportion of free fatty acids produced within a cell, especially plant cells. Plant cells having such a modified free fatty acid composition are also contemplated herein.

Methods to further increase the medium-chain fatty acid content of plant seed oils from plants engineered to contain medium-chain acyl-ACP thioesterase are provided in an additional embodiment. In particular use of antisense sequences associated with plant long-chain thioesterases are used to decrease the native plant long-chain thioesterases, thus providing greater substrate availability for the medium-chain thioesterase.

Other aspects of this invention relate to methods for using a plant medium-chain thioesterase. Expression of a plant medium-chain thioesterase in a bacterial cell to produce medium-chain fatty acids is provided. By this method, quantities of such fatty acids may be harvested from bacteria. Exemplified in the application is the use of *E. coli* expressing elm and Cuphea thioesterases; the fadD *E. coli* mutant is preferred in some applications. In addition, temperature ranges for improved medium-chain fatty acid production are described.

Similarly, non-plant enzymes having medium-chain acyl-ACP thioesterase activity are useful in the plant and bacteria expression methods discussed. In particular, an acyl transferase from *Vibrio harvei*, is useful in applications for production of C14 medium-chain fatty acids.

Methods to produce an unsaturated medium-chain thioesterase by the use of a plant medium-chain thioesterase are also described herein. It is now found that, even in plants which exclusively produce and incorporate quantities of saturated medium-chain acyl-ACP fatty acids into triglycerides, the thioesterase may have activity against unsaturated fatty acids of the same length.

DESCRIPTION OF THE FIGURES

FIG. 1. The nucleic acid sequence and translated amino acid sequence of a bay C12:0-ACP thioesterase cDNA clone (SEQ ID NO:1), are provided.

FIG. 2. The nucleic acid sequence and translated amino acid sequence of an elm C10:0-ACP thioesterase partial cDNA clone (SEQ ID NO:2), are provided.

FIG. 3. DNA sequence of a PCR fragment of a Cuphea thioesterase gene (SEQ ID NO:3), is presented. Translated amino acid sequence in the region corresponding to the Cuphea thioesterase gene is also shown.

FIG. 4. DNA sequences of *C. hookeriana* C93A PCR fragments from clones 14-2 (SEQ ID NO:4) and 14-9 (SEQ ID NO:5), are provided.

FIG. 5. Preliminary DNA sequence and translated amino acid sequence from the 5' end of a *Cuphea hookeriana* thioesterase (CUPH-1) cDNA clone (SEQ ID NO:6), is shown.

FIG. 6. The entire nucleic acid sequence and the translated amino acid sequence of a full length *Cuphea hookeriana* thioesterase (CUPH-1) cDNA clone, CMT9 (SEQ ID NO:7), is shown.

FIG. 7. The nucleic acid sequence and the translated amino acid sequence of a full length *Cuphea hookeriana* thioesterase (CUPH-2) cDNA clone, CMT7 (SEQ ID NO:8), is shown.

FIG. 8. The nucleic acid sequence of a *Cuphea hookeriana* thioesterase cDNA clone, CMT13 (SEQ ID NO:9), is shown.

FIG. 9. The nucleic acid sequence a of a *Cuphea hookeriana* thioesterase cDNA clone, CMT10 (SEQ ID NO:10), is shown.

FIG. 10. The nucleic acid sequence and translated amino acid sequence of a *Cuphea hookeriana* thioesterase cDNA clone, CLT7 (SEQ ID NO:11), is shown.

FIG. 11. Nucleic acid sequence and translated amino acid sequence of a *Brassica campestris* long-chain acyl ACP thioesterase clone (SEQ ID NO:12), is shown.

DETAILED DESCRIPTION OF THE INVENTION

Plant thioesterases, including medium-chain plant thioesterases are described in WO 91/16421 (PCT/US91/02960), WO 92/20236 (PCT/US92/04332) and U.S. Ser. No. 07/824,247 which are hereby incorporated by reference in their entirety.

A plant medium-chain thioesterase of this invention includes any sequence of amino acids, peptide, polypeptide or protein obtainable from a plant source which demonstrates the ability to catalyze the production of free fatty acid(s) from C8–C14 fatty acyl-ACP substrates under plant enzyme reactive conditions. By "enzyme reactive conditions" is meant that any necessary conditions are available in an environment (i.e., such factors as temperature, pH, lack of inhibiting substances) which will permit the enzyme to function. Of particular interest in the instant application are C8 and C10 preferring acyl-ACP thioesterases obtainable from *Cuphea hookeriana* and elm (an Ulmus species).

Plant thioesterases are obtainable from the specific exemplified sequences provided herein and from related sources. For example, several species in the genus Cuphea accumulate triglycerides containing medium-chain fatty acids in their seeds, e.g., procumbens, lutea, hookeriana, hyssopifolia, wrightii and inflata. Another natural plant source of medium-chain fatty acids are seeds of the Lauraceae family: e.g., Pisa (*Actinodophne hookeri*) and Sweet Bay (*Laurus nobilis*). Other plant sources include Myristicaceae, Simarubaceae, Vochysiaceae, and Salvadoraceae, and rainforest species of Erisma, Picramnia and Virola, which have been reported to accumulate C14 fatty acids.

As noted above, plants having significant presence of medium-chain fatty acids therein are preferred candidates to obtain naturally-derived medium-chain preferring plant thioesterases. However, it should also be recognized that other plant sources which do not have a significant presence of medium-chain fatty acids may be readily screened as other enzyme sources. In addition, a comparison between endogenous medium-chain preferring plant thioesterases and between longer and/or shorter chain preferring plant thioesterases may yield insights for protein modeling or other modifications to create synthetic medium-chain preferring plant thioesterases as well as discussed above.

Additional enzymes having medium-chain acyl-ACP thioesterase activity are also described herein which are obtained from non-plant sources, but which may be modified and combined with plant sequences for use in constructs for plant genetic engineering applications. Furthermore, such sequences may be used for production of medium-chain fatty acids in procaryotic cells, such as described herein for bay thioesterase.

One skilled in the art will readily recognize that antibody preparations, nucleic acid probes (DNA and RNA) and the like may be prepared and used to screen and recover "homologous" or "related" thioesterases from a variety of plant sources. For immunological screening methods, antibody preparations either monoclonal or polyclonal are utilized. For detection, the antibody is labeled using radioactivity or any one of a variety of second antibody/enzyme conjugate systems that are commercially available. Examples of some of the available antibody detection systems are described by Oberfilder (*Focus* (1989) BRL Life Technologies, Inc., 11:1–5).

Homologous sequences are found when there is an identity of sequence, which may be determined upon comparison of sequence information, nucleic acid or amino acid, or through hybridization reactions between a known thioesterase and a candidate source. Conservative changes, such as Glu/Asp, Val/Ile, Ser/Thr, Arg/Lys and Gln/Asn may also be considered in determining amino acid sequence homology. Amino acid sequences are considered homologous by as little as 25% sequence identity between the two complete mature proteins. (See generally, Doolittle, R. F., OF URFS and ORFS (University Science Books, Calif., 1986.) Typically, a lengthy nucleic acid sequence may show as little as 50–60% sequence identity, and more preferably at least about 70% sequence identity, between the target sequence and the given plant thioesterase of interest excluding any deletions which may be present, and still be considered related.

A genomic or other appropriate library prepared from the candidate plant source of interest may be probed with conserved sequences from plant thioesterase to identify homologously related sequences. Shorter probes are often particularly useful for polymerase chain reactions (PCR), especially when highly conserved sequences can be identified.

When longer nucleic acid fragments are employed (>100 bp) as probes, especially when using complete or large cDNA sequences, one would screen with low stringencies (for example 40°–50° C. below the melting temperature of the probe) in order to obtain signal from the target sample with 20–50% deviation, i.e., homologous sequences. (See, Beltz, et al. *Methods in Enzymology* (1983) 100:266–285.).

Using methods known to those of ordinary skill in the art, a DNA sequence encoding a plant medium-chain thioesterase can be inserted into constructs which can be introduced into a host cell of choice for expression of the enzyme, including plant cells for the production of transgenic plants. Thus, potential host cells include both prokaryotic and eukaryotic cells. A host cell may be unicellular or found in a multicellar differentiated or undifferentiated organism depending upon the intended use. Cells of this invention may be distinguished by having a plant thioesterase foreign to the wild-type cell present therein, for example, by having a recombinant nucleic acid construct encoding a plant thioesterase therein.

Also, depending upon the host, the regulatory regions will vary, including regions from viral, plasmid or chromosomal genes, or the like. For expression in prokaryotic or eukaryotic microorganisms, particularly unicellular hosts, a wide variety of constitutive or reulatable promoters may be employed. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, when expression in a plant host cell is desired, the constructs will involve regulatory regions (promoters and termination regions) functional in plants. The open reading frame, coding for the plant thioesterase or functional fragment thereof will be joined at its 5' end to a transcription initiation regulatory region such as the wild-type sequence naturally found 5' upstream to the thioesterase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for CaMV 35S and nopaline and mannopine synthases, or with napin, ACP promoters and the like. The transcription/translation initiation regions corresponding to such structural genes are found immediately 5' upstream to the respective start codons. If a particular promoter is desired, such as a promoter native to the plant host of interest or a modified promoter, i.e., having transcription initiation regions derived from one gene source and translation initiation regions derived from a different gene source, including the sequence encoding the plant thioesterase of interest, or enhanced promoters, such as double 35S CaMV promoters, the sequences may be joined together using standard techniques. For most applications desiring the expression of medium-chain thioesterases in plants, the use of seed specific promoters are preferred.

It is noted that such constructs have been successfully used in genetic engineering applications to produce C12 (laurate) in plants which do not normally contain such medium-chain fatty acids (WO 91/16421). In particular, a bay C12 preferring acyl-ACP thioesterase was expressed in Brassica and Arabidopsis plants. Seeds from the resulting plants were observed to contain up to 50 mole percent laurate in the seed oils (WO 92/20236).

A further genetic engineering approach to increase the medium-chain fatty acid production in such transgenic plants utilizes antisense sequence of the native long-chain thioesterase in the target host plant. In this manner, the amount of long-chain thioesterase is decreased. As a result, the introduced medium-chain thioesterase has increased available substrate and the content of medium-chain fatty acids produced may be similarly increased.

Other genetic engineering approaches to increase medium-chain fatty acids would include insertion of additional DNA sequence encoding plant thioesterase structural genes into cells, use of transcriptional initiation regions evidencing higher mRNA copy numbers or an improved timing specificity profile which corresponds better to the availability of substrate, for example. For example, analysis of the time course of laurate production, under regulatory control of a napin promoter, in seeds of a Brassica plant demonstrates that the appearance of medium-chain trioesterase activity lags behind the onset of storage oil synthesis by approximately 5–7 days. Calculations show that about 20% of the total fatty acids are already synthesized before the medium-chain thioesterase makes significant impact. Thus, substantially higher medium-chain fatty acid levels (10–20%) might be obtained if the thioesterase gene is expressed at an earlier stage of embryo development Additionally, means to increase the efficiency of translation may include the use of the complete structural coding sequence of the medium-chain thioesterase gene. Thus, use of the complete 5'-region of the medium-chain thioesterase coding sequence may improve medium-chain fatty acid production.

When a plant medium-chain thioesterase is expressed in a bacterial cell, particularly in a bacterial cell which is not capable of efficiently degrading fatty acids, an abundance of medium-chain fatty acids can be produced and harvested from the cell. Similarly, over production of non-plant enzymes having acyl-ACP thioesterase activity is also useful for production of medium-chain fatty acids in *E. coli*. In some instances, medium-chain fatty acid salts form crystals which can be readily separated from the bacterial cells. Bacterial mutants which are deficient in acyl-CoA synthase, such as the *E. coli* fadD and fadE mutants, may be employed.

In studies with bay thioesterase, growth of fadD bay thioesterase transformants relative to the vector transformed control was severely retarded at 37° C., and less so at 25°–30° C. Liquid cultures growing at the lower temperatures accumulated a precipitate and colonies formed on petri dishes at 25° C. deposit large quantities of laurate crystals, especially at the surface. These deposits, as identified by FAB-mass spectrometry were identified as laurate. An abnormal growth rate phenotype is also noted in *E. coli* cells expressing an elm medium-chain preferring acyl-ACP thioesterase. At 37° C., the elm thioesterase appears to be toxic to the cells, and at 25° C. or 30° C. the cells grow much more slowly than control non-transformed cells. It has been noted with both bay and elm thioesterase-expressing *E. coli* cells that variants which grow at the same rate as control cells at 25° C. or 30° C. may be selected when the transformed cells are grown for several generations. In addition, when a bay thioesterase-expressing normal growth phenotype variant is cured of the bay thioesterase encoding plasmid and retransformed with a similar plasmid containing the elm thioesterase expression construct, the elm thioesterase expressing cells exhibit a normal growth phenotype in the first generation of cells comprising the construct. Similarly, myristate crystals are produced in fadD *E. coli* transformants expressing a Vibrio C14 thioesterase gene. In this instance the growth temperature does not significantly effect cell growth or myristate production. After separation and quantitation by gas chromatography, it is estimated that the laurate crystals deposited by the fadD-bay thioesterase transformants on petri dises represented about 30–100% of the total dry weight of the producing bacteria.

When expression of the medium-chain thioesterase is desired in plant cells, various plants of interest include, but are not limited to, rapeseed (Canola and High Erucic Acid varieties), sunflower, safflower, cotton, Cuphea, soybean, peanut, coconut and oil palms, and corn. Depending on the method for introducing the recombinant constructs into the host cell, other DNA sequences may be required. Importantly, this invention is applicable to dicotyledyons and monocotyledons species alike and will be readily applicable to new and/or improved transformation and regulation techniques.

In any event, the method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

The medium-chain fatty acids produced in the transgenic host cells of this invention are useful in various commercial applications. For example, C12 and C14 are used extensively in the detergent industry. C8 and C10 fatty acids are used as lubricants, for example in jet engines. C8 and C10 fatty acids also find use in high performance sports foods and in low calorie food applications.

The following examples are provided by way of illustration and not by limitation.

EXAMPLES

Example 1

Sources of Plant C8 and C10 Acyl-ACP Thioesterases

Discovery of a C10 preferring acyl-ACP thioesterase activity in developing seeds from *Cuphea hookeriana* is described in WO 91/16421. Other plants may also be sources of desirable thioesterases which have preferences for fatty acyl chain lengths of C8 or C10. Such additional plant thioesterases may be identified by analyzing the triacylglyceride composition of various plant oils and the presence of a specific thioesterase confirmed by assays using the appropriate acyl-ACP substrate. The assay for C10 preferring acyl-ACP thioesterase, as described for example in WO 91/16421, may be used for such analyses.

For example, other plants which are now discovered to have desirable thioesterase enzymes include elm (Ulmaceae) and coconut (*Cocos nucifera*). A significant percentage of 10:0 fatty acids are detected in elm seeds, and both 8:0 and 10:0 fatty acids are prominent in seeds from coconut. Results of biochemical assays to test for thioesterase activity in developing embryos from elm and coconut are presented below in Table 1.

TABLE 1

| | Activity (mean cpm in ether extract) | |
|---|---|---|
| Substrate | elm | coconut |
| 8:0-ACP | 84 | 784 |
| 10:0-ACP | 2199 | 1162 |
| 12:0-ACP | 383 | 1308 |
| 14:0-ACP | 1774 | 573 |
| 16:0-ACP | 3460 | 902 |
| 18:1-ACP | 3931 | 2245 |

With elm, a peak of thioesterase activity is seen with the C10:0-ACP substrate, in addition to significant activity with longer-chain substrates. This evidence suggests that a thioesterase with specific activity towards C10:0-ACP substrate is present in elm embryos. With coconut, endosperm thioesterase activity is seen with C8:0, C10:0, C12:0 and C14:0 medium-chain substrates, as shown in Table 6. These activities accord with the considerable C8:0, C10:0, C12:0, and C14:0 fatty acyl contents of the endosperm oil suggesting that one or more thioesterases with activity on these medium chain acyl-ACPs are present in coconut endosperm and responsible for medium chain formation therein.

Example 2

Acyl-ACP Thioesterase cDNA Sequences

A. Bay

Sequence of a full length bay C12 preferring acyl-ACP cDNA clone, pCGN3822, (3A-17), is presented in FIG. 1.

The N-terminal sequence of the mature bay thioesterase, isolated from the developing seeds, has been reported as beginning at amino acid residue 84 of the derived protein sequence (WO 92/20236). The remaining N-terminal amino acids would therefore be expected to represent sequence of a transit peptide. This 83 amino acid sequence has features common to plastid transit peptides, which are usually between 40 and 100 amino acids long (Keegstra et al., *Ann. Rev. Plant Physiol.* and *Plant Mol. Biol.* (1989) 40:471–501). A hydropathy plot of this transit peptide region reveals a hydrophobic domain at each end of the transit sequence. Other transit peptide sequences have been shown to contain similar hydrophobic N-terminal domains. The significance of this N-terminal domain is not known, but certain experiments suggest that lipid-mediated binding may be important for plastid import of some proteins (Friedman and Keegstra, *Plant Physiol.* (1989) 89:993–999). As to the C-terminal domain, comparison of hydropathy plots of known imported chloroplastic stromal protein transit peptides (Keegstra et al, supra) indicates that these transit peptides do not have a hydrophobic domain at the C-terminus. However, preproteins destined to the thylakoid lumen of the chloroplast have an alanine-rich hydrophobic domain at the C-terminal end of their transit peptides (Smeekens et al., TIBS (1990) 15:73–76). The existence of such a domain in the transit sequence of the bay thioesterase might suggest that it has a double-domain transit peptide targeting this enzyme to the lumen of the thylakoid equivalent or to the intermembrane space. This is unexpected, since the substrate, acyl-ACP, has been detected in the stroma (Ohlrogge et al., *Proc. Nat. Acad. Sci.* (1979) 76:1194–1198). An alternative explanation for the existence of such a domain in the bay thioesterase preprotein is that it may represent a membrane anchor of the mature protein that is cleaved upon purification, leading to a sequence determination of an artificial N-terminus. The in vivo N-terminus of the mature thioesterase protein would then lie at a location further upstream than indicated by amino acid sequence analysis.

Analysis of additional plant medium-chain acyl-ACP thioesterase sequences, such as those encoded by the elm and Cuphea clones described herein, indicates extensive homology in the region initially identified as the C-terminal domain of the bay C12 preferring acyl-ACP thioesterase transit peptide. It is thus possible that this postulated transit peptide "C-terminal domain" in fact represents a further N-terminal region of the mature bay thioesterase. In such a case, the leucine residue indicated as amino acid number 60 in FIG. 1 is a candidate for the N-terminus of the mature bay C12 thioesterase protein. Western analysis of transgenic Brassica plants expressing the bay C12 thioesterase protein reveals a protein band of approximately 41 kD, which size is consistent with the suggestion that the mature protein N-terminus is located at or near the leucine residue, amino acid number 60.

Gene bank searches with the derived amino acid sequences of plant medium-chain preferring acyl-ACP thioesterases do not reveal significant matches with any entry, including the vertebrate medium-chain acyl-ACP thioesterase II (Naggert et al., *Biochem. J.* (1987) 243:597–601). Also, the plant medium-chain preferring acyl-ACP thioesterases do not contain a sequence resembling the fatty acid synthetase thioesterase active-site motif (Aitken, 1990 in *Identification of Protein Concensus Sequences, Active Site Motifs, Phosphorylation and other Post-translational Modifications* (Ellis Horwood, Chichester, West Sussex, England, pp. 40–147).

B. Cuphea

DNA sequence encoding a portion of a *Cuphea hookeriana* thioesterase protein (FIG. 3) may be obtained by PCR as described in WO 92/20236.

Additional DNA sequences corresponding to Cuphea thioesterase peptide regions are obtained by PCR using degenerate olgonucleotides designed from peptide fragments from conserved regions of plant thioesterases described in WO 92/20236. A forward primer, TECU9, contains 17 nucleotides corresponding to all possible coding sequences for amino acids 176–181 of the bay and camphor thioesterase proteins. A reverse primer, TECU3A, contains 18 nucleotides corresponding to the complement of all possible coding sequences for amino acids 283–288 of the bay and camphor thioesterase proteins, In addition, the forward and reverse primers contain BamHI or XhoI restriction sites, respectively, at the 5' end, and the reverse primer contains an inosine nucleotide at the 3' end. The safflower, bay and camphor sequences diverge at two amino acid positions in the forward primer region, and at one amino acid residue in the reverse primer region. The degeneracy of oligonucleotide primers is such that they could encode the safflower, bay and camphor sequences.

Polymerase chain reaction samples (100 μl) are prepared using reverse transcribed *Cuphea hookeriana* RNA as template and 1 μM of each of the oligonucleotide primers. PCR products are analyzed by agarose gel electrophoresis, and an approximately 300 bp DNA fragment, the predicted size from the thioesterase peptide sequences, is observed. The DNA fragment, designated C93A (Cuphea) is isolated and cloned into a convenient plasmid vector using the PCR-inserted BamHI and XhoI restriction digest sites. DNA sequence of representative clones is obtained. Analysis of these sequences indicates that at least two different, but homologous *Cuphea hookeriana* cDNAs were amplified. The DNA sequences of two Cuphea PCR fragments, 14-2 and 14-9, are presented in FIG. 4.

Total RNA for cDNA library construction may be isolated from developing Cuphea embryos by modifying the DNA isolation method of Webb and Knapp (*Plant Mol. Biol. Reporter* (1990) 8:180–195). Buffers include:

REC: 50 mM TrisCl pH 9, 0.7M NaCl, 10 mM EDTA pH8, 0.5% CTAB.

REC+: Add B-mercaptoethanol to 1% immediately prior to use.

RECP: 50 mM TrisCl pH9, 10 mM EDTA pH8, and 0.5% CTAB.

RECP+: Add B-mercaptoethanol to 1% immediately prior to use.

For extraction of 1 g of tissue, 10 ml of REC+ and 0.5 g of PVPP is added to tissue that has been ground in liquid nitrogen and homogenized. The homogenized material is centrifuged for 10 min at 1200 rpm. The supernatant is poured through miracloth onto 3 ml cold chloroform and homogenized again. After centrifugation, 12,000 RPM for 10 min, the upper phase is taken and its volume determined. An equal volume of RECP+ is added and the mixture is allowed to stand for 20 min. at room temperature. The material is centrifuged for 20 min. at 10,000 rpm twice and the supernatant is discarded after each spin. The pellet is dissolved in 0.4 ml of 1M NaCl (DEPC) and extracted with an equal volume of phenol/chloroform. Following ethanol precipitation, the pellet is dissolved in 1 ml of DEPC water. Poly (A) RNA may be isolated from this total RNA according to Maniatis et al. (*Molecular Cloning: A Laboratory Manual* (1982) Cold Springs Harbor, N.Y.). cDNA libraries may be constructed in commercially available plasmid or phage vectors.

The thioesterase encoding fragments obtained by PCR as described above are labeled and used to screen Cuphea cDNA libraries to isolate thioesterase cDNAs. Preliminary DNA sequence of a Cuphea cDNA clone TAA 342 is presented in FIG. 5. Translated amino acid sequence of the Cuphea clone from the presumed mature N-terminus (based on homology to the bay thioesterase) is shown.

The sequence is preliminary and does not reveal a single open reading frame in the 5' region of the clone. An open reading frame believed to represent the mature protein sequence is shown below the corresponding DNA sequence. The N-terminal amino acid was selected based on homology to the bay thioesterase protein.

Additional Cuphea cDNA clones were obtained by screening a cDNA library prepared using a Uni-ZAP (Stratagene) phage library cloning system. The library was screening using radiolabeled TAA 342 DNA. The library was hybridized at 42° C. using 30% formamide, and washing was conducted at low stringency (room temperature with 1× SSC, 0.1% SDS). Numerous thioesterase clones were identified and DNA sequences determined. Three classes of Cuphea cDNA clones have been identified. The original TAA 342 clone discussed above is representative of CUPH-1 type clones which have extensive regions of homology to other plant medium-chain preferring acyl-ACP thioesterases. Nucleic acid sequence and translated amino acid sequence of a CUPH-1 clone, CMT9, is shown in FIG. 6. The mature protein is believed to begin either at or near the leucine at amino acid position 88, or the leucine at amino acid position 112. From comparison of TAA 342 to CMT9, it is now believed that the TAA 342 sequence is missing a base which if present would shift the reading frame of the TAA 342 CUPH-1 clone to agree with the CUPH-1 thioesterase encoding sequence on CMT9. In particular, the stop codon for CUPH-1 is now believed to be the TAG triplet at nucleotides 1391–1393 of FIG. 5.

DNA sequence of an additional CUPH-1 clone, CMT10, is shown in FIG. 9. CMT10 has greater than 90% sequence identity with CMT9, but less than the approximately 99% sequence identity noted in fragments from other CUPH-1 type clones.

A second class of Cuphea thioesterase cDNAs is identified as CUPH-2. These cDNAs also demonstrate extensive homology to other plant medium-chain acyl-ACP thioesterases. Expression of a representative clone, CMT7, in *E. coli* (discussed in more detail below), indicates that CUPH-2 clones encode a medium-chain preferring acyl-ACP thioesterase protein having preferential activity towards C8 and C10 acyl-ACP substrates. DNA sequence and translated amino acid sequence of CMT7 is shown in FIG. 7.

Preliminary DNA sequence from the 5' end of an additional CUPH-2 clone, CMT13, is shown in FIG. 8. Although CMT13 demonstrates extensive sequence identity with CMT7. DNA sequence alignment reveals several gaps, which together total approximately 48 nucleotides, where the CMT13 clone is missing sequences present in the CMT7 clone.

DNA sequence analysis of a third class of Cuphea thioesterase cDNA clones indicates extensive homology at the DNA and amino acid level to 18:1 acyl-ACP thioesterases from Brassica (FIG. 11) and safflower (WO 92/20236). DNA sequence and translated amino acid sequence of a representative clone, CLT2, is shown in FIG. 10.

C. Elm

Elm acyl-ACP thioesterase clones may also be obtained using PCR primers for plant thioesterase sequences as discussed above for Cuphea. TECU9 and TECU3A are used in PCR reactions using reverse transcribed RNA isolated from elm embryos as template. As with Cuphea, an approximately 300 nucleotide fragment, E93A, is obtained and used to probe an elm cDNA library. Nucleic acid sequence and translated amino acid sequence of an elm medium-chain preferring acyl-ACP thioesterase clone are shown in FIG. 2. The clone encodes the entire mature elm thioesterase protein, but appears to be lacking some of the transit peptide encoding region. By comparison with other plant medium-chain acyl-ACP thioesterases, the mature elm protein is believed to begin either at the leucine indicated as amino acid number 54, or at the aspartate indicated as amino acid number 79.

Example 3

Expression of Acyl-ACP Thioesterases In *E. coli*

A. Expression of elm thioesterase.

An elm acyl-ACP thioesterase cDNA clone is expressed in *E. coli* as a lacZ fusion. The ULM1 cDNA clone, KA10, represented in FIG. 2 is digested with StuI and XbaI to produce an approximately 1000 base pair fragment containing the majority of the mature elm thioesterase encoding sequence. The StuI site is located at nucleotides 250–255 of the sequence shown in FIG. 2, and the XbaI site is located at nucleotides 1251–1256, 3' to the stop codon. As discussed above, the N-terminus for the mature elm thioesterase is believed to be either the leucine residue encoded by nucleotides 160–162 or the aspartate residue encoded by nucleotides 235–237. The StuI/XbaI fragment is inserted into StuI/XbaI digested pUC118 resulting in construct KA11. For expression analysis, KA11 is used to transform *E. coli* strain DH5 å or an *E. coli* mutant, fadD, which lacks medium-chain specific acyl-CoA synthetase (Overath et al., *Eur. J. Biochem* (1969) 7:559–574).

As has been observed with bay thioesterase constructs, *E. coli* clones expressing the elm thioesterase exhibited abnormal growth rate and morphology phenotypes. The growth rate of *E. coli* DH5 å ($fadD^+$) or fadD mutant cells expressing the elm thioesterase is initially much slower than growth of control cells at either 25° C. or 30° C. At 37° C., the elm thioesterase plasmid appears to be toxic to the *E. coli* cells. After growing the transformed cultures for several generations, variants may be selected which grow at the same rate as control cells at 25° C. or 30° C. A similar result was seen with fadD cells comprising bay thioesterase expression constructs. A fadD mutant strain selected as having a normal growth rate when expressing the bay thioesterase was cured of the bay thioesterase construct and transformed with the elm thioesterase construct. This strain exhibits a normal growth phenotype in the first generation of cells comprising the elm thioesterase construct.

For thioesterase activity and fatty acid composition assays, a 25–50 ml culture of *E. coli* cells containing the elm thioesterase construct, and a similar culture of control cells are grown at 25° C. to an $OD_{600}$ of ~0.5. Induction of the thioesterase expression may be achieved by the addition of IPTG to 0.4 mM followed by 1 or 2 hours further growth. For slow growing cultures, longer growth periods may be required following addition of IPTG.

A ten-ml aliquot of each culture (containing cells plus the culture medium) is assayed for specific activity towards C10:0-ACP and C16:0-ACP substrates as follows. Cells are harvested by centrifugation, resuspended in 0.5 ml assay buffer and lysed by sonication. Cell debris may be removed by further centrifugation. The supernant is then used in thioesterase activity assays as per Pollard et al., *Arch. Biochem & Biophys.* (1991) 281:306–312 using C10:0-ACP and C16:0-ACP substrates.

The activity assays from normal growth phenotype KA11 cells reproducibly demonstrate differentially elevated C10:0-ACP and C16:0-ACP hydrolysis activities. Upon induction with IPTG, the C10:0-ACP and C16:0-ACP activities are affected differently. The specific activity of the C16:0-ACP hydrolysis decreases slightly, while that of the C10:0-ACP hydrolase increases by approximately 44%. This data suggests that the C16:0-ACP hydrolysis activity is derived from the *E. coli* cells, rather than the elm thioesterase. As discussed in more detail below, a similar C16:0-ACP hydrolysis activity is detected in *E. coli* cells transformed with a *Cuphea hookeriana* thioesterase clone, CUPH-1.

For analysis of the fatty acid composition, a 4.5 ml sample of *E. coli* cells grown and induced as described above is transferred into a 15 ml glass vial with a teflon-lined cap. 100 µl of a 1 mg/ml standards solution containing 1 mg/ml each of C11:0 free fatty acid, C15:0 free fatty acid, and C17:0 TAG in 1:1 chloroform/methanol is added to the sample, followed by addition of 200 µl of glacial acetic acid and 10 ml of 1:1 chloroform/methanol. The samples are vortexed to mix thoroughly and centrifuged for 5 minutes at 1000 rpm for complete phase separation. The lower (chloroform) phase is carefully removed and transferred to a clean flask appropriate for use in a rotary evaporator (Rotovap). The sample is evaporated to near dryness. As medium-chain fatty acids appear to evaporate preferentially after solvent is removed, it is important to use just enough heat to maintain the vials at room temperature. The dried samples are methanolyzed by adding 1 ml of 5% sulfuric acid in methanol, transferring the samples to a 5 ml vial, and incubating the sample in a 90° C. water bath for 2 hours. The sample is allowed to cool, after which 1 ml of 0.9% NaCl and 300 µl of hexane are added. The sample is vortexed to mix thoroughly and centrifuged at 1000 rpm for 5 minutes. The top (hexane) layer is carefully removed and placed in a plastic autosampler vial with a glass cone insert, followed by capping of the vial with a crimp seal.

The samples are analyzed by gas-liquid chromatography (GC) using a temperature program to enhance the separation of components having 10 or fewer carbons. The temperature program used provides for a temperature of 140° C. for 3 minutes, followed by a temperature increase of 5° C./minute until 230° C. is reached, and 230° C. is maintained for 11 minutes. Samples are analyzed on a Hewlett-Packard 5890 (Palo Alto, Calif.) gas chromatograph. Fatty acid content calculations are based on the internal standards.

GC analysis indicates that the slow growing *E. coli* DH 5å cells expressing the elm thioesterase contained approximately 46.5 mole % C10:0 and 33.3 mole % C8:0 fatty acids as compared to fatty acid levels in control cultures of 1.8 mole % C10:0 and 3.1 mole % C8:0. The largest percentage component of the control culture was C16:0 at 45.2 mole %. In comparison, the KA11 culture contained only approximately 8.4 mole % C16:0. Similar analyses on a later generation of KA11 cells which exhibited a normal growth rate phenotype, revealed lower percentages of C10:0, 25.9 mole %, and C8:0, 18.9 mole %, fatty acids. In this later study, the control *E. coli* culture contained approximately 5 mole % each of C10:0 and C8:0.

B. Expression of *Cuphea hookeriana* thioesterases.

1. The CUPH-2 type *C. hookeriana* cDNA clone shown in FIG. 7 (CMT7) is expressed as a lacZ fusion in *E. coli*. CMT7 is digested with StuI and partially digested with XhoI, and the approximately 1100 base pair fragment containing the majority of the thioesterase encoding region is cloned into SmaI/SalI digested pUC118, resulting in construct KA17. The StuI site in CMT7 is located at nucleotides 380–385 of the sequence shown in FIG. 7, and the XhoI site is located following the 3' end of the cDNA clone in the vector cloning region. As discussed above, the N-terminus for the mature CUPH-2 thioesterase is believed to be either the aspartate residue encoded by nucleotides 365–367 or the leucine residue encoded by nucleotides 293–295. For expression analysis, KA17 is used to transform *E. coli* $fadD^+$ cells (commercially available cells such as SURE cells from BRL may be used) or an *E. coli* mutant, fadD, which lacks medium-chain specific acyl-CoA synthetase (Overath et al., *Eur. J. Biochem* (1969) 7:559–574).

Unlike the results with bay and elm, *E. coli* $fadD^+$ cells transformed with KA17 exhibit no unusual growth or morphology phenotype. However, in fadD mutants, the plasmid is not maintained at 37° C. At 30° C., the transformed cells grow slightly slower and form smaller colonies on media plates although the plasmid is stably maintained.

GC analysis is conducted on cultures of both $fadD^+$ and fadD mutant strains expressing KA17 thioesterase. An increase in C8:0 and to a lesser extent C10:0 fatty acid accumulation is observed in both $fadD^+$ and fadD mutant strains. In one experiment, levels of C8:0 and C10:0 fatty acyl groups in $fadD^+$ cells following a 2 hour induction were 23.5 and 8.1 mole % respectively. Levels of C8:0 and C10:0 fatty acyl groups after 2 hour induction in control cells were 3.9 and 3.0 mole % respectively. In a fadD mutant strain, fatty acids were measured following overnight induction. In cells transformed with KA17 , C8:0 and C10:0 levels were 51.5 and 14.3 mole % respectively. In control cells C8:0 and C10:0 levels were 2.3 and 2.5 mole % respectively.

2. A construct for expression of a *Cuphea hookeriana* CUPH-1 type thioesterase in *E. coli* is also prepared. The construct encodes a lacZ fusion of the Cuphea mature protein sequence shown in FIG. 5. The fusion protein is expressed in both wild-type (K12) and fadD strains of *E. coli* . Both strains of *E. coli* deposit large amount of crystals when transformed with the Cuphea expression construct. In addition, both transformed strains exhibit growth retardation, which is slight in the K-12 cells and severe in the fadD mutants. The slow growth phenotype is believed due to a toxic effect of C8 and C10 fatty acids on the *E. coli* cells. Fatty acid analysis (acid methanolysis) of K12 and fadD transformants does not indicate accumulation of a particular fatty acid. It is believed that the crystals observed in these cells may represent an altered form of a medium chain fatty acid that is not detectable by the acid methanolysis methods utilized. Studies of the ability of the cell extracts to hydrolyze acyl-ACP substrates indicates increased acyl-ACP activity towards medium chain fatty acyl-ACP C8 , C10 and C12 substrates in transformed fadD cells. Results of these analyses are shown in Table 2.

TABLE 2

| Lysate | Substrate | Hydrolysis Activity |
|---|---|---|
| Cuphea clone | 8:0-ACP | 830 |
| " | 10:0-ACP | 1444 |
| " | 12:0-ACP | 1540 |
| " | 14:0-ACP | 1209 |
| " | 18:1-ACP | 1015 |
| control | 8:0-ACP | 4 |
| " | 10:0-ACP | 52 |
| " | 12:0-ACP | 63 |
| " | 14:0-ACP | 145 |
| " | 18:1-ACP | 128 |

Normalization of the assay results to the C18:1 levels reveals a significant increase in the C8:0, C10:0 and C12:0-ACP thioesterase activities.

Further analyses of fast growing variants expressing the CUPH-1 thioesterase were conducted. Isolation and analysis of the crystals produced by the CUPH-1 expressing *E. coli* cells indicates that these crystals are comprised of predominantly C16 and C14 fatty acids. In addition, further analyses revealed an increase in hydrolysis activity towards C16 fatty acids in these cells. It is not clear if the C16 activity and fatty acid production are a direct result of the CUPH-1 thioesterase, or if this effect is derived from the *E. coli* cells.

C. Expression of Myristoyl ACP Thioesterase in *E. coli*

A *Vibrio harvei* myristoyl ACP thioesterase encoding sequence (Miyamoto et al., *J. Biol. Chem.* (1988) 262:13393–13399) lacking the initial ATG codon is prepared by PCR. The gene is expressed in *E. coli* as a lacZ fusion and *E. coli* extracts are assayed to confirm myristoyl ACP thioesterase activity. The C14 thioesterase construct is used to transform an *E. coli* fadD strain. The cells transformed in this manner deposit large quantities of crystals which are identified as potassium myristate by mass spectrometry. Fatty acid analysis of the *E. coli* extracts reveals that greater than 50% (on a mole basis) of the fatty acids are C14:0, as compared to control *E. coli* fadD cells which contain approximately 11.5 mole percent C14:0.

Example 4

Constructs for Plant Transformation

Constructs for expression of Cuphea and elm thioesterases in plant cells which utilize a napin expression cassette are prepared as follows.

A. Napin Expression Cassette

A napin expression cassette, pCGN1808, is described in copending U.S. patent application Ser. No. 07/742,834 which is incorporated herein by reference. pCGN1808 is modified to contain flanking restriction sites to allow movement of only the expression sequences and not the antibiotic resistance marker to binary vectors. Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restriction sites as well as nucleotides 408–423 of the napin 5'-sequence (from the EcoRV site) and the reverse primer contains the complement to napin sequences 718–739 which include the unique SacI site in the 5'-promoter. The PCR was performed using in a Perkin Elmer/Cetus thermocycler according to manufacturer's specifications. The PCR fragment is subcloned as a blunt-ended fragment into pUC8 (Vieira and Messing (1982) *Gene* 19:259–268) digested with HincII to give pCGN3217. Sequenced of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3' noncoding regions.

B. Cuphea Acyl-ACP Thioesterase Expression Construct

PCR analysis of *Cuphea hookeriana* reverse transcribed cDNA indicated that the 5' region of the TAA 342 CUPH-1 clone was lacking a guanine nucleotide (G) following nucleotide 144 of the sequence shown in FIG. 5. (DNA sequence analysis of the CMT9 CUPH-1 clone confirms the presence of the G nucleotide in that region.) Thus, a G nucleotide was inserted after nucleotide 144 in TAA 342 by PCR directed mutagenesis resulting in an encoding region beginning at the ATG at 143–145 of the sequence shown in FIG. 5. The corrected encoding sequence was cloned into a convenient vector using SalI and XhoI sites (also inserted in the PCR reaction), resulting in KA2. A SalI fragment of the resulting clone, comprising nucleotides 137–1464 of the sequence shown in FIG. 5 (plus the inserted G nucleotide discussed above), was cloned into napin expression cassette pCGN3223. The napin/Cuphea thioesterase/napin construct was then excised as a HindIII fragment and cloned into the binary vector pCGN1557 (McBride and Summerfelt (1990) *Plant Mol. Biol.* 14:269–276). The resulting construct, pCGN4800, was transformed into *Agrobacterium tumefaciens* and used to prepare transformed plants.

Similarly, the Cuphea CUPH-2 clone, CMT-7 is inserted into a napin expression cassette and the resulting napin 5'/CUPH-2/napin 3' construct transferred to a binary vector for plant transformation.

C. Elm Acyl-ACP Thioesterase Expression Construct

A construct for expression of an elm C10 and C8 acyl-ACP thioesterase in plant seed cells using a napin expression cassette is prepared as follows. As discussed above, the elm ULM-1 medium-chain acyl-ACP thioesterase cDNA does not appear to encode the entire thioesterase transit peptide. Thus, the elm thioesterase coding region was fused to the transit peptide encoding region from the Cuphea CUPH-1 clone as follows. pCGN4800 (CUPH-1 in napin cassette) was digested with XbaI, blunted and digested with StuI to remove the mature protein coding portion of the CUPH-1 construct. The StuI site is located at nucleotides 496–501 of the CUPH-1 sequence shown in FIG. 5. The XbaI site is located between the end of the Cuphea thioesterase cDNA sequence and the napin 3' regulatory region. The ULM-1 mature protein encoding region is inserted into the napin/Cuphea transit peptide backbone resulting from removal of the Cuphea mature protein endoding region as follows. The ULM-1 clone is digested with XbaI, blunted and digested with StuI to obtain the elm thioesterase mature protein encoding region. The StuI site is located at nucleotides 250–255 of the sequence shown in FIG. 2, and the XbaI site is located at nucleotides 1251–1256, 3' to the stop codon. Ligation of the elm StuI/XbaI fragment into the napin/Cuphea transit peptide backbone results in pCGN4802, having the napin 5'/Cuphea transit:elm mature/napin 3' expression construct. pCGN4803 is transferred to pCGN1557 as a HindIII fragment resulting in pCGN4803, a binary construct for plant transformation.

Example 5

Plant Transformation

A variety of methods have been developed to insert a DNA sequence of interest into the genome of a plant host to obtain the transcription or transcription and translation of the sequence to effect phenotypic changes.

A. Brassica Transformation

Seeds of *Brassica napus* cv. Westar are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyriodoxine (50 μg/l), nicotinic acid (50 μg/l), glycine (200 μg/l), and 0.6% Phytagar (Gibco) pH 5.8. Seeds are germinated in a Percival chamber at 22° C. in a 16 h photoperiod with cool fluorescent and red light of intensity approximately 65μ Einsteins per square meter per second ($\mu Em^{-2}S^{-1}$).

Hypocotyls are excised from 5–7 day old seedlings, cut into pieces approximately 4 mm in length, and plated on feeder plates (Horsch et al., *Science* (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg $KH_2PO_4$ with 3% sucrose, 2,4-D (1.0 mg/l), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu Em^{-2}S^{-1}$ to Single colonies of *A. tumefaciens* strain EHA 101 containing a binary plasmid are transferred to 5 ml MG/L broth and grown overnight at 30° C. Hypocotyl explants are immersed in 7–12 ml MG/L broth with bacteria diluted to $1\times10^8$ bacteria/ml and after 10–25 min. are placed onto feeder plates. Per liter MG/L broth contains 5 g mannitol, 1 g L-Glutamic acid or 1.15 g sodium glutamate, 0.25 g $kH_2PO_4$, 0.10 g NaCl, 0.10 g $MGSO_4.7H_2O$, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/l.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for thioesterase activity.

B. Arabidposis Transformation

Transgenic *Arabidopsis thaliana* plants may be obtained by Agrobacterium-mediated transformation as described by Valverkens et al., (*Proc. Nat. Acad. Sci.* (1988) 85:5536–5540). Constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187).

C. Peanut Transformation

DNA sequences of interest may be introduced as expression cassettes, comprising at least a promoter region, a gene of interest, and a termination region, into a plant genome via particle bombardment as described in European Patent Application 332 855 and in co-pending application U.S. Ser. No. 07/225,332, filed Jul. 27, 1988.

Briefly, tungsten or gold particles of a size ranging from 0.5 μM–3 μM are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers.

The bombardment of the tissue with the DNA-coated particles is carried out using a Biolistics™ particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 μM to 300 μM.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15:473) (MS plus 2.0 mg/l 6-benzyladenine (BA) for the cotyledon segments) and incubated in the dark for 1 week at 25°±2° C. and are subsequently transferred to continuous cool white fluorescent light (6.8 $W/m^2$). On the 10th day of culture, the plantlets are transferred to pots containing sterile soil, are kept in the shade for 3–5 days are and finally moved to greenhouse.

The putative transgenic shoots are rooted. Integration of exogenous DNA into the plant genome may be confirmed by various methods know to those skilled in the art.

Example 7

Transformation with Antisense Plant Thioesterase

Constructs for expression of antisense Brassica thioesterase in plant cells are prepared as follows. An approximately 1.1 kb fragment of the full length Brassica long chain thioesterase is obtained by PCR amplification of the pCGN3266 insert. The forward primer binds to the antisense strand and primes synthesis of the sense thioesterase sequence. This primer contains nucleotides 27–42 of the pCGN3266 sequence shown in FIG. 6A, and also has an XhoI restriction site at the 5' end. The reverse primer binds to the sense strand and primes synthesis of antisense thioesterase DNA. It contains the reverse complement to nucleotides 1174–1191 of the pCGN3266 sequence shown in FIG. 6A, and also has a SalI restriction site at the 5' end.

PCR reactions are run using Taq polymerase in a DNA thermocycler (Perkin Elmer/Cetus) according to manufacturer's specifications. Cycle parameters may be altered to provide a maximum yield of the thioesterase PCR product. The 1.1 kb PCR product is verified by restriction mapping and agarose gel electrophoresis. The PCR product is digested with XhoI and SalI restriction enzymes and cloned into the napin expression casette pCGN3233 which has been digested with XhoI and SalI.

The napin/antisense thioesterase/napin plasmid generated by these manipulations is digested to obtain the napin/antisense thioesterase/napin fragment, which is inserted into binary vectors for plant transformation. For re-transformation of transgenic laurate-producing plants having a kanamycin resistance marker, the fragment is inserted into a hygromycin binary vector as follows. The fragment, containing ~1.7 kb of napin 5' noncoding sequence, an ~1.1 kb SalI/XhoI antisense thioesterase cDNA fragment and ~1.5 kb of 3' napin non-coding region, is engineered to contain KpnI recognition sequences at the ends. The fragment is then digested with KpnI and ligated to KpnI digested pCGN2769 (hygromycin binary vector discussed above) for plant transformation.

For transformation of non-transgenic Brassica, the napin/antisense BTE/napin fragment may be obtained by digestion with KpnI and partial digestion with BamHI to generate an ~3.3 kb fragment containing ~1.7 kb of napin 5' noncoding sequence, the ~1.1 kb SalI/XhoI antisense thioesterase cDNA fragment and ~0.33 kb of the 3' napin noncoding region, the rest of the napin 3' region having been deleted due to the BamHI site in this region. The ~3.3 kb KpnI/BamHI fragment may be ligated to KpnI/BamHI digested pCGN1578 to provide a plant transformation vector.

In addition to the above Brassica antisense thioesterase construct, other constructs having various portions of the Brassica thioesterase encoding sequence may be desirable. As there are regions of homology between the bay and Brassica thioesterase sequences, the possibility of decreasing the bay thioesterase expression with the antisense Brassica sequence may be avoided by using fragments of the Brassica gene which are not substantially homologous to the bay gene. For example, the sequences at the 5' and 3' ends of the Brassica clone are not significantly homologous to the bay sequence and are therefore desirable for antisense Brassica thioesterase purposes.

Example 7

Expression of Non-Plant ACYL-ACP Thioesterases In Plants

Constructs for expression of the *Vibrio harvei* myristoyl ACP thioesterase in plant cells which utilize napin promoter regions are prepared as follows. Two 100 base oligos are synthesized:

HARV-S: 5' CGG TCT AGA T AA CAA TCA ATG CAA GAC TAT TGC ACA CGT GTT GCG TGT GAA CAA TGG TCA GGA GCT TCA CGT CTG GGA AAC GCC CCC AAA AGA AAA CGT G (SEQ ID NO:13) 3'

HARV-A: 5' ATA CTC GGC CAA TCC AGC GAA GTG GTC CAT TCT TCT GGC GAA ACC AGA AGC AAT CAA AAT GGT GTT GTT TTT AAA AGG CAC GTT TTC TTT TGG GGG CGT T (SEQ ID NO:14) 3'

The two oligos contain a region of complementary sequence for annealing (underlined region). A TAQ polymerase extension reaction utilizing the two oligos yields a 180 bp product. The oligos consisted essentially of luxD sequence with sequence changes introduced to remove the 3 potential poly(A) addition sites and to alter 5 bases to change the codon preference from bacteria to plants. All changes were conservative; i.e. the amino acid sequence was not altered.

The 180 bp TAQ polymerase extension product is blunted and cloned into Bluescript. The approximately 180 bp luxD fragment is then removed from Bluescript by digestion with XbaI and EaeI and cloned in frame with the EaeI/XbaI fragment from the Vibrio cDNA clone, containing the remainder of the luxD gene, by 3-way ligation into XbaI/XhoI digested Bluescript SK. The luxD gene is removed by digestion with XbaI and partial digestion with PstI and cloned in frame with the safflower thioesterase transit peptide encoding region into a napin expression casette. The napin 5'/safflower transit:myristoyl ACP thioesterase/napin 3' fragment is cloned into KpnI/BamHI digested pCGN1557 (McBride and Summerfelt, supra) resulting in pCGN3845, a binary expression vector for plant transformation.

The resulting transgenic plants are grown to seed and analyzed to determine the percentage of C14 fatty acids produced as the result of insertion of the bacterial acyl transferase gene. Analysis of pooled seed samples from 24 segregating transgenic (T1) *Brassica napus* plants indicates C14 fatty acid levels ranging from 0.12 to 1.13 mole %. Two plants, 3845-1 and 3845-18, contain greater than 1 mole % C14:0 fatty acids in their seed oils. Similar analysis of non-transgenic *B. napus* seeds reveals C14:0 levels of approximately 0.1 mole %. Analysis of single seeds from 3845-18 reveals individual seeds having greater than 2 mole % C14:0 in the oil. Western analysis is conducted to determine amounts of the C14:0 thioesterase present in transgenic plants. A comparison of protein amount to mole % C14:0 (myristate) produced indicates that myristate levels increase with increasing amounts of the thioesterase protein.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A recombinant DNA construct comprising a plant medium-chain preferring acyl-ACP thioesterase encoding sequence, wherein said thioesterase has hydrolysis activity towards C8 and C10 fatty acyl-ACP substrates.

2. The construct of claim 1 encoding a precursor plant medium-chain preferring acyl-ACP thioesterase.

3. The construct of claim 1 wherein said plant is *Cuphea hookeriana*.

4. A recombinant DNA construct comprising an expression cassette capable of producing a plant medium-chain preferring acyl-ACP thioesterase in a host cell, wherein said construct comprises, in the 5' to 3' direction of transcription, a transcriptional initiation regulatory region functional in said host cell, a translational initiation regulatory region functional in said host cell, a DNA sequence encoding a biologically active plant medium-chain preferring acyl-ACP thioesterase having activity towards C8 and C10 fatty acyl-ACP substrates, and a transcriptional and translational termination regulatory region functional in said host cell, wherein said plant thioesterase encoding sequence is under the control of said regulatory regions.

5. The construct of claim 4 wherein said host cell is a plant cell.

6. The construct of claim 5 wherein said transcriptional initiation region is obtained from a gene preferentially expressed in plant seed tissue.

7. The construct of claim 4 wherein said sequence is obtainable from *Cuphea hookeriana*.

8. The construct of claim 4 wherein said sequence is from a *Cuphea hookeriana* CUPH-2 thioesterase gene.

9. A host cell comprising a plant thioesterase encoding sequence construct of claim 4.

10. The cell of claim 9 wherein said cell is a plant cell.

11. The cell of claim 10 wherein said plant cell is a Brassica plant cell.

12. A transgenic host cell comprising an expressed plant medium-chain preferring acyl-ACP thioesterase having activity towards C8 and C10 fatty acyl-ACP substrates.

13. The cell of claim 12 wherein said host cell is a plant cell.

14. A method of producing C8 and C10 fatty acids in a plant host cell, wherein said method comprises:

growing a plant cell having integrated into its genome a DNA construct, said construct comprising in the 5' to 3' direction of transcription, a transcriptional regulatory region functional in said plant cell and a plant medium-chain preferring acyl-ACP thioesterase encoding sequence, under conditions which will permit the expression of said plant thioesterase, wherein said plant thioesterase has activity towards C8 and C10 fatty acyl-ACP substrates.

15. The method of claim 14 wherein said plant cell is an oilseed embryo plant cell.

16. The method of claim 14 wherein said plant thioesterase encoding sequence is obtainable from *Cuphea hookeriana*.

17. The method of claim 14 wherein said plant thioesterase encoding sequence is from a *Cuphea hookeriana* CUPH-2 thioesterase gene.

18. A plant cell having a modified fatty acid composition produced according to the method of claim 14.

19. The construct of claim 8 wherein said sequence encodes the *Cuphea hookeriana* acyl-ACP thioesterase protein shown in FIG. 7 (SEQ ID NO:8).

20. The construct of claim 8 wherein said sequence comprises the *Cuphea hookeriana* acyl-ACP thioesterase encoding sequence shown in FIG. 7 (SEQ ID NO:8).

* * * * *